US012806152B2

(12) United States Patent
Gill et al.

(10) Patent No.: US 12,806,152 B2
(45) **Date of Patent: *Nov. 24, 2026**

(54) TARGETING JUNCTIONAL EPITHELIUM IN THE GINGIVAL CREVICE FOR IMMUNE MODULATION

(71) Applicant: Texas Tech University System, Lubbock, TX (US)

(72) Inventors: Harvinder Singh Gill, Lubbock, TX (US); Akhilesh K. Shakya, Lubbock, TX (US); Rohan S. J. Ingrole, Lubbock, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/186,888

(22) Filed: Apr. 23, 2025

(65) Prior Publication Data

US 2025/0248947 A1 Aug. 7, 2025

Related U.S. Application Data

(63) Continuation of application No. 17/909,480, filed as application No. PCT/US2022/039536 on Aug. 5, 2022.

(Continued)

(51) Int. Cl.

*A61K 9/70* (2006.01)
*A61K 9/00* (2006.01)

(Continued)

(52) U.S. Cl.

CPC .............. *A61K 9/70* (2013.01); *A61K 9/0063* (2013.01); *A61K 39/145* (2013.01); *A61K 39/35* (2013.01);

(Continued)

(58) Field of Classification Search

CPC ...... A61K 9/70; A61K 9/0063; A61K 39/145; A61K 39/35; A61K 2039/5252;

(Continued)

(56) References Cited

U.S. PATENT DOCUMENTS

| | | |
|---|---|---|
| 5,284,648 A | 2/1994 | White et al. |
| 5,874,798 A | 2/1999 | Wiegele et al. |

(Continued)

FOREIGN PATENT DOCUMENTS

| | | |
|---|---|---|
| EP | 1792627 | 6/2007 |
| JP | 5683804 | 6/2011 |

(Continued)

OTHER PUBLICATIONS

Bosshardt et al. "The Junctional Epithelium: from Health to Disease" in Critical Review in Oral Biology & Medicine, J Dent Res 84(1):9-20, 2005. (Year: 2005).*

(Continued)

*Primary Examiner* — Blessing M Fubara
(74) *Attorney, Agent, or Firm* — Edwin S. Flores; Daniel J. Chalker; Chalker Flores, LLP

(57) ABSTRACT

The present invention includes a method of activating, modulating, and/or anergizing an immune response by targeting the junctional epithelia in the gingival crevice.

10 Claims, 19 Drawing Sheets

Related U.S. Application Data

(60) Provisional application No. 63/229,784, filed on Aug. 5, 2021.

(51) Int. Cl.

| | |
|---|---|
| ***A61K 39/00*** | (2006.01) |
| ***A61K 39/145*** | (2006.01) |
| ***A61K 39/35*** | (2006.01) |
| ***A61P 31/16*** | (2006.01) |
| ***C12N 7/00*** | (2006.01) |

(52) U.S. Cl.
CPC ................ *A61P 31/16* (2018.01); *C12N 7/00* (2013.01); *A61K 2039/5252* (2013.01); *A61K 2039/542* (2013.01); *A61K 2039/55561* (2013.01); *C12N 2760/16134* (2013.01); *C12N 2760/16171* (2013.01)

(58) Field of Classification Search
CPC .... A61K 2039/542; A61K 2039/55561; A61P 31/16; C12N 7/00; C12N 2760/16134; C12N 2760/16171
See application file for complete search history.

(56) References Cited

U.S. PATENT DOCUMENTS

| | | | | |
|---|---|---|---|---|
| 5,875,798 | A | 3/1999 | Petrus | |
| 5,875,799 | A | 3/1999 | Petrus | |
| 6,270,890 | B1 | 8/2001 | Curtis et al. | |
| 6,289,904 | B1 | 9/2001 | Suhonen et al. | |
| 6,541,011 | B2 | 4/2003 | Punnonen et al. | |
| 7,398,784 | B2 | 7/2008 | Ochs et al. | |
| 9,271,899 | B2 * | 3/2016 | Francois | A61Q 11/00 |
| 2001/0006624 | A1 | 7/2001 | Witt et al. | |
| 2006/0110709 | A1 | 5/2006 | Clark, Jr. | |
| 2009/0155296 | A1 | 6/2009 | Levine | |
| 2010/0291127 | A1 | 11/2010 | Eisenbach et al. | |
| 2012/0132555 | A1 | 5/2012 | Lavrova | |
| 2013/0095154 | A1 | 4/2013 | McHale et al. | |
| 2019/0091292 | A1 * | 3/2019 | Jeong | G01N 33/53 |
| 2020/0121430 | A1 * | 4/2020 | Cavaliere | A61C 15/046 |
| 2020/0138941 | A1 | 5/2020 | Gill et al. | |
| 2021/0228848 | A1 | 7/2021 | Gill et al. | |
| 2023/0042036 | A1 | 2/2023 | Syn et al. | |

FOREIGN PATENT DOCUMENTS

| | | |
|---|---|---|
| RU | 2470647 | 12/2012 |
| WO | 88/06594 | 9/1988 |
| WO | 1999032046 | 7/1999 |
| WO | 2010132954 | 11/2010 |
| WO | 2016093815 | 6/2016 |
| WO | 2019213298 | 11/2019 |

OTHER PUBLICATIONS

Allam, J.-P., et al., "Distribution of Langerhans cells and mast cells within the human oral mucosa: new application sites of allergens in sublingual immunotherapy?" Allergy (2008), 63:720-727.

Hovav, A.-H., "Dendritic cells of the oral mucosa," Mucosal Immunology (2014), 7:27-37.

International Search Report & Written Opinion, PCT/US2023/034134 [ISA/US] dated Mar. 11, 2024.

International Search Report and Written Opinion [ISR/US] PCT/US2022/039536 dated Dec. 23, 2022.

Moutsopoulos, N. M., and J. E. Konkel, "Tissue-Specific Immunity at the Oral Mucosal Barrier," Trends in Immunology (2018), 39(4):276-287.

* cited by examiner

○ PE+CpG coated floss ● PE coated floss ▲ Untreated ▼ Naive mice with challenge only

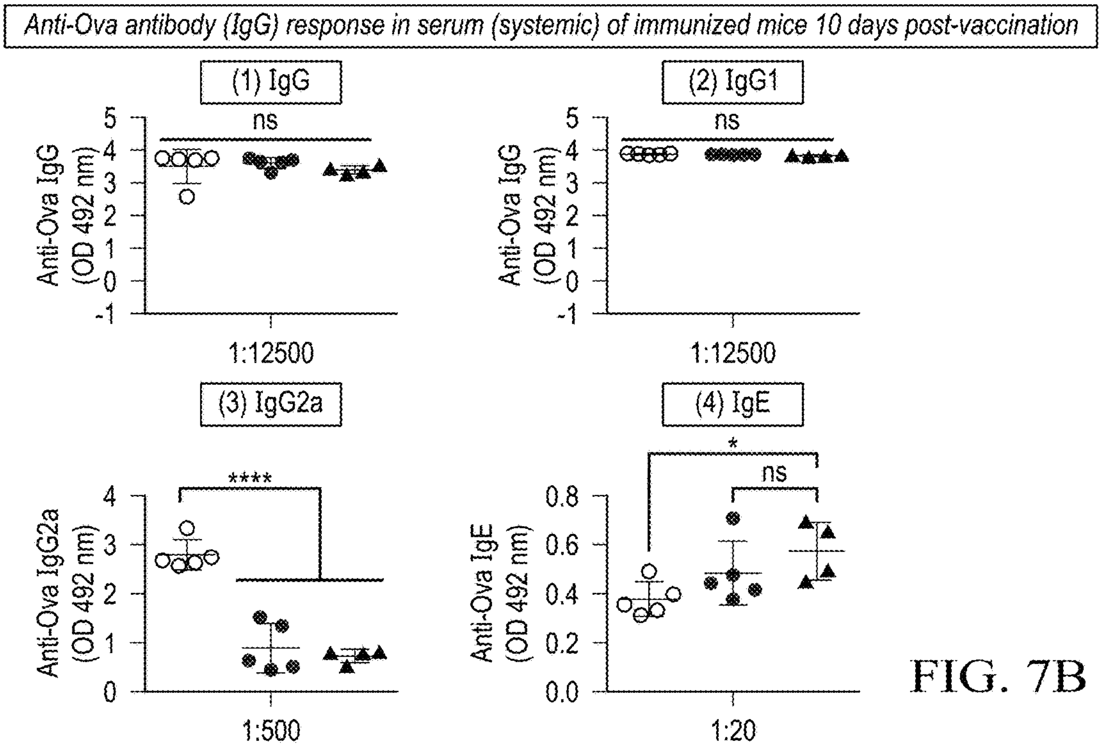
FIG. 7B
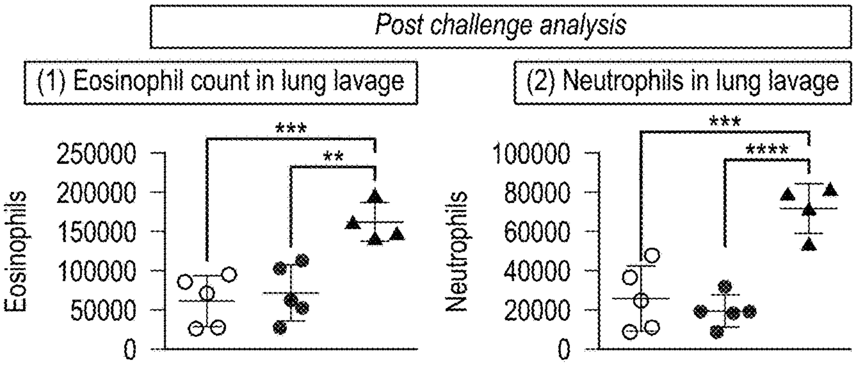
FIG. 7C
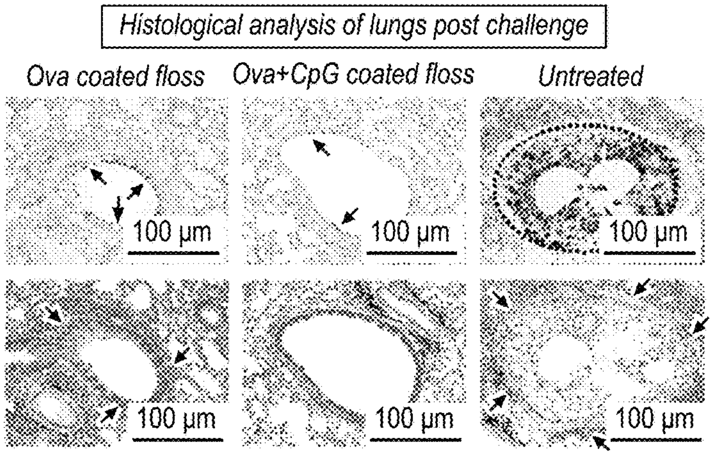
FIG. 7D

Floss coated with four different food colors (blue, green, yellow, red)

Side '1'. Ova-sulfo deposited over length

Side '2', (back-side) of same floss deposited over length with M2e-hold+CpG

Twisted floss to show depositions from both sides

TARGETING JUNCTIONAL EPITHELIUM IN THE GINGIVAL CREVICE FOR IMMUNE MODULATION

CROSS-REFERENCE TO RELATED APPLICATIONS

This patent application claims priority to and is a continuation application of U.S. Ser. No. 17/909,480, filed Sep. 6, 2022, which is the National Stage of International Application No. PCT/US2022/039536, filed on Aug. 5, 2022 claiming the priority of U.S. Provisional Application Ser. No. 63/229,784, filed Aug. 5, 2021, the entire contents of which are incorporated herein by reference.

STATEMENT OF FEDERALLY FUNDED RESEARCH

This invention was made with government support under R01AI135197 and R01AI137846 awarded by the National Institutes of Health. The government has certain rights in the invention.

TECHNICAL FIELD OF THE INVENTION

The present invention relates in general to the field of targeting the immune response, and more particularly, to targeting the junctional epithelium (JE) in the gingival crevice for vaccination against infectious agents, allergen immunotherapy, and immune modulation for autoimmune diseases.

INCORPORATION-BY-REFERENCE OF MATERIALS FILED ON COMPACT DISC

None.

BACKGROUND OF THE INVENTION

Without limiting the scope of the invention, its background is described in connection with immunizations and allergen immunotherapy.

Tooth eruption through the gingiva creates a break in an otherwise continuous and uninterrupted human mucosal surface. To seal this discontinuity, the gingival tissue attaches to each tooth through the junctional epithelium. The junctional epithelium is attached to the tooth and forms a seal between the oral cavity and the underlying tissues. The junctional epithelium seal is leaky and has high permeability because it is only a few cell layers thick and has wide intercellular spaces amongst these cells. The gingival tissue beyond this zone of attachment forms the gingival crevice. The high permeability of the junctional epithelium, a characteristic not seen elsewhere within the mucosal system, offers easy passage to commensal bacteria, potential pathogens, and food allergens. The gingival niche has an extensive network of immune cells, including both innate and adaptive immune cells such as neutrophils, natural killer cells, macrophages, dendritic cells, CD4+/CD8+ T cells, B cells, and innate lymphoid cells. This network helps to defend and create immune responses against the constant stimulation by microbes, allergens, and food proteins.

Mucosal surfaces are the first point of contact with the environment and thus naturally serve as portals of entry for a vast majority of pathogens and allergens. For example, the coronavirus causing the current pandemic is transmitted primarily through respiratory mucosa, HIV is transmitted primarily through reproductive and gastrointestinal mucosa, pollens which cause respiratory allergies initiate contact at the respiratory mucosa, and peanut a food allergen initiates first contact in the oral cavity mucosa. It is recognized and widely reported in literature that a strong mucosal and systemic immune response is more effective at combating infections as compared to just a systemic immune response. However, vaccine delivery via injections does not stimulate a strong mucosal immunity, it only stimulates a strong systemic immunity. To generate strong mucosal immunity and strong systemic immunity vaccines must be delivered through mucosal surfaces. However, mucosal surfaces are designed to keep material out, thus merely placing vaccines on top of the mucosal surface does not lead to their efficient uptake. For example, to treat allergies, a mucosal delivery approach has received attention and it is called sublingual immunotherapy (SLIT) in which the allergen is placed under the tongue of the patient for about one minute to stimulate the oral cavity mucosa. Tablets containing grass and pollen allergens that utilize the SLIT approach have recently been approved by the FDA to treat allergic rhinitis caused by pollen and grass allergies. In SLIT, since the uptake through the mucosa under tongue is inefficient about 50-100 fold higher allergen amount is required as compared to injections, and the variability of patient response is high. As another example, oral vaccination by ingestion of the vaccine, which essentially helps to place the vaccine on top of the gastrointestinal mucosa has low efficacy because the stomach's high acidic environment and enzyme rich environment can damage the vaccine, and also the tough barrier provided by the gastrointestinal mucosa prevents efficient transport of the vaccine through the mucosal lining into underlying tissue layers. Therefore, it is understood that to obtain efficient immune responses, the mucosal barrier should be breached to deliver molecules through the mucosal surfaces and into the underlying tissue; simply placing the molecules on top of the mucosal surfaces does not lead to efficient immune responses. To achieve improved uptake and transport of molecules, different approaches such as encapsulation of molecules in micro and nanoparticles and relying on uptake of particles via cells, use of chemicals to disrupt the mucosal barriers to improve transport, use of infective viruses and bacteria and change of pH or mechanical methods are used.

One such prior art patent is U.S. Pat. No. 9,271,899, issued to Francois, and entitled "Methods, articles and kits for allergic desensitization, via the oral mucosa", which is said to teach Compositions and methods of use for desensitizing a subject to an allergen via regions of the oral mucosa are provided, specifically, targeting vestibular mucosa to cause oral immune tolerance.

Despite these advancements, a need remains for novel immune targeting strategy that maximizes the dosing of antigen to trigger a robust immune response.

SUMMARY OF THE INVENTION

As embodied and broadly described herein, an aspect of the present disclosure relates to a method of modulating an immune response in a subject (e.g., human being/s and pets (such as dog, cat, cows, pigs or other domesticated animals) comprising: delivering an effective amount of one or more antigens, immunogens, allergens, or combinations thereof into a gingival crevice, specifically targeting junctional epithelium (JE), wherein the amount is sufficient to activate or modulate an immune response. In one aspect, the one or more antigens, immunogens, allergens, or combinations thereof are not delivered to the vestibular mucosa. In another aspect, the modulating of the immune response is activating or anergizing an immune response by targeting a junctional epithelia in the gingival crevice. In another aspect, the one or more antigens, immunogens, allergens, or combinations thereof are provided to maximize delivery of the one or more antigens, immunogens, allergens, or combinations thereof into the gingival crevice. In another aspect, the method further comprises adding one or more agents that increase the permeability of the one or more antigen into the gingival crevice (GC). In another aspect, between 0.001%-100% of the one or more antigens, immunogens, allergens, or combinations thereof, is in a depot at a junctional epithelium (JE) of the gingival crevice. In another aspect, the one or more antigens, immunogens, allergens, or combinations thereof are provided repeatedly to the junctional epithelium (JE) of the gingival crevice. In another aspect, delivery of the one or more antigens, immunogens, allergens, or combinations thereof to the JE is before or after consumption of a food or drink. In another aspect, the one or more antigens, immunogens, allergens, or combinations thereof is applied 1, 2, 3, 4, 5, or 6 times daily or weekly. In another aspect, two or more antigens, immunogens, allergens, or combinations thereof, are delivered to a junctional epithelium (JE) of the gingival crevice. In another aspect, the one or more antigens, immunogens, allergens, or combinations thereof desensitize the individual to the one or more antigens, immunogens, allergens, or combinations thereof by 10%, 20%, 30%, 40%, 50%, 60%, 70%, 80%, 90% or 100%. In another aspect, the one or more antigens, immunogens, allergens, or combinations thereof desensitize the subject to the one or more antigens, immunogens, allergens, or combinations thereof by between 0.1-100%. In another aspect, delivery of the one or more antigens, immunogens, allergens, or combinations thereof to the JE is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more before the subject eats food, drinks water, or both. In another aspect, delivery of the one or more antigens, immunogens, allergens, or combinations thereof to the JE is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more after the subject eats food, drinks water, or both. In another aspect, the amount of antigens, immunogens, allergens, or combinations thereof delivered to the junctional epithelium ranges from picograms to milligrams. In another aspect, the immune response is an activating, modifying, or an anergizing immune response.

As embodied and broadly described herein, an aspect of the present disclosure relates to a method of triggering an immune response in a subject comprising: providing an effective amount of one or more antigens, immunogens, allergens, or combinations thereof into a gingival crevice, specifically targeting junctional epithelium (JE), wherein the amount is sufficient to trigger an immune response to the one or more antigens, immunogens, allergens, or combinations thereof; wherein the one or more antigens, immunogens, allergens, or combinations thereof are embedded, coated, or attached to a delivery device that targets a junctional epithelium at a gingival crevice. In one aspect, the one or more antigens, immunogens, allergens, or combinations thereof are not delivered to the vestibular mucosa. In another aspect, the triggering of the immune response is activating or anergizing an immune response by targeting a junctional epithelium in the gingival crevice. In another aspect, the delivery device has a thickness less than 5 mm, preferably less than 3 mm, and preferably less than 1 mm. In another aspect, the delivery device comprises natural or synthetic polymers, organic materials, metals, inorganic material(s) or combinations thereof. In another aspect, the delivery device comprises a mucoadhesive layer or a hydrophobic layer or a hydrophilic layer or a combination. In another aspect, the delivery device comprises a microporous structure allowing diffusion of antigen to gingival crevice. In another aspect, the device comprises a system/device designed to reach the gingival crevice, an interdental brush or bristles. In another aspect, the amount of antigens, immunogens, allergens, or combinations thereof delivered to the junctional epithelium ranges from picograms to milligrams. In another aspect, the one or more antigens, immunogens, allergens, or combinations thereof desensitize the individual to the one or more antigens, immunogens, allergens, or combinations thereof by 10%, 20%, 30%, 40%, 50%, 60%, 70%, 80%, 90% or 100%. In another aspect, the one or more antigens, immunogens, allergens, or combinations thereof desensitize the subject to the one or more antigens, immunogens, allergens, or combinations thereof by between 0.1-100%. In another aspect, delivery of the one or more antigens, immunogens, allergens, or combinations thereof to the J E is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more before the subject eats food, drinks water, or both. In another aspect, delivery of the one or more antigens, immunogens, allergens, or combinations thereof to the JE is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more after the subject eats food, drinks water, or both. In another aspect, an increase in the immune response is an increase in an activating, modifying, or anergizing an immune response. In another aspect, the immune response targets at least one of: a bacteria, a virus, a fungi, a protozoan, a parasite, a prion, a toxin, a cancer, an allergy, or an auto-immune diseases. In another aspect, the one or more antigens is selected from at least one of: proteins, peptides, deoxyribonucleic acid (DNA) oligonucleotides, ribonucleic acid (RNA) oligonucleotides, broken cells, intact cells, lipids, toxin variants, carbohydrates, virus-like particles, liposomes, live attenuated or killed natural or recombinant microorganisms, virosomes, polymeric/inorganic/organic micro and nanoparticles, or immune stimulating complexes (ISCOMS). In another aspect, the one or more antigens comprises a peptide obtained from a cancer cell or portion thereof selected from T- and B cell lymphoproliferative diseases, ovarian cancer, pancreatic cancer, head and neck cancer, squamous cell carcinoma, gastrointestinal cancer, breast cancer, prostate cancer or non-small cell lung cancer. In another aspect, the one or more antigen include a food allergen selected from peanut, shellfish, egg protein, milk protein, legumes, nuts, or an airway allergen selected from a house dust mite or pollen. In another aspect, the one or more antigens is/are at least one of attached, adsorbed, or anchored physically or chemically to a dental floss or thin device or to a strip/patch or an interdental brush with thickness suitable for its placement into the gingival crevice. In another aspect, the composition further comprises one or more adjuvants selected from a cytokine, chemokine, toll-like receptor ligands or activators, alum, muramyl dipeptides, pyridine, chitosan, saponins, oils, emulsions, bacterial cell wall extracts, bacterial proteins, cytoplasmic bacterial DNA or mimics, viral RNA or mimics, synthetic oligonucleotides, stimulator of interferon (IFN) genes (STING) agonists (2'3'-cGAMP, c-di-AMP, 2'3'-c-di-AM(PS)2 (Rp,RP), c-di-GM P, CL401, CL413, CL429, Flagellin, Imiquimod, LPS-EB, MPLA, ODN 1585, ODN 1826, ODN2006, ODN2395, pam3CSK 4, poly(I:C), R848, TDB), natural polymer (poly-γ-glutamic acid, chitosan, mannan, lipomannan, lentinan, dextran), synthetic polymer (poly-N-isopropylacrylamide, copolymers, block polymers, polyphosphazenes, polyelectrolytes, polyanhydrides, polymethacrylates, polyglycolic-co-lactide, polycaprolactones, polyvinylpyrrolidone, cationic polymers) and combinations thereof. In another aspect, the one or more antigen(s) activate(s) an innate immune response, an adaptive immune response, or both.

As embodied and broadly described herein, an aspect of the present disclosure relates to an immunization comprising an effective amount of one or more antigens, immunogens, allergens, or combinations thereof on a delivery device that targets a junctional epithelium at a gingival crevice, wherein an amount of the one or more antigens, immunogens, allergens, or combinations thereof is sufficient to activate or modulate an immune response. In one aspect, the one or more antigens, immunogens, allergens, or combinations thereof are not delivered to the vestibular mucosa. In another aspect, the modulating of the immune response is activating or anergizing an immune response by targeting a junctional epithelia in the gingival crevice. In another aspect, the one or more antigens, immunogens, allergens, or combinations thereof are provided to maximize delivery of the one or more antigens, immunogens, allergens, or combinations thereof into the gingival crevice. In another aspect, the immunization further comprises one or more agents that increase the permeability of the one or more antigens, immunogens, allergens, or combinations thereof into the gingival crevice (GC). In another aspect, between 0.001%-100% of the one or more antigens, immunogens, allergens, or combinations thereof, is in a depot at a junctional epithelium (JE) of the gingival crevice. In another aspect, the immunization further comprises one or more pharmaceutically acceptable carriers, excipients, diluents, buffers, or salts.

In another aspect, the one or more active agents (one or more antigens, immunogens, allergens, or combinations thereof) improves health conditions by enhancing pharmacodynamics/pharmacokinetics of an active agent by targeting junctional epithelia in the gingival crevice.

As embodied and broadly described herein, an aspect of the present disclosure relates to a method of making a floss that comprises a pre-determined amount of one or more active agents comprising: providing a floss; and depositing on the floss an active agent in a pharmacologically acceptable carrier containing a pre-determined amount of the active agent. In one aspect, the deposition process deposits on a single contiguous portion of the floss, or on two or more discrete portions of the floss with same or different spacing between the each said deposited region. In one aspect, the deposition process comprises placing liquid drops on the floss, or dragging the liquid drop(s) on the floss to spread it over a certain distance/length on the floss using a pipette, or spray depositing, or ink jet depositing, or pipette based depositing, or cartridge depositing or a combination thereof. In one aspect, the viscosity of the material deposited is 0.01 centipoise (cp), 1 cp, 10 cp, 100 cp, 1000 cp, 10000 cp, 100000 cp, 200000 cp, 300000 cp, 500000 cp, 1000000, or 100000000 cp. In one aspect the deposition process is manual or automated or semi-automated or a combination thereof. In another aspect the deposition is done on one side of the floss or both sides of the floss. In one aspect, each adjacent deposition comprises the same active agent or a different active agent, or each adjacent deposition comprises the same active agent in a different concentration/amount; or wherein each adjacent deposition comprises a different active agent in a different concentration; or each adjacent deposition is placed on a different side/plane from the adjacent deposition; or each adjacent deposition is placed on an opposite side of the floss from the adjacent deposition; or adjacent deposition each comprise a different active agent from a prior adjacent deposition. In another aspect the deposition of different active agents is done on one side of the floss or on both sides of the floss. In another aspect the deposition of an active agent is done on one side of the floss or on both sides of the floss with each side comprising same or different concentration/amount of the active agent. In one aspect, each adjacent deposition comprises the same active agent or a different active agent deposited on top of one another. In another aspect, the active agents are deposited on opposite sides over the same or different distance/lengths. In another aspect, each adjacent deposition comprises of a different active agent with a different solvent requirement for solubility (for example, one active agent with water as a solvent whereas the other active agent with organic solvent requirement); or each adjacent deposition is placed on a different side/plane from the adjacent deposition; or each adjacent deposition is placed on an opposite side of the floss from the adjacent deposition; or adjacent deposition each comprise a different active agent with a different solvent requirement from a prior adjacent deposition that has different solvent requirement. In another aspect, the active agents with different solvent requirements are deposited on opposite sides over the same or different distance/lengths. In another aspect, the active agents with same solvent requirement are deposited on top of one another with the same or different distance/lengths. In another aspect, the active agents with different solvent requirement are deposited on top of one another with the same or different distance/lengths. In another aspect, the floss is solid, frayed, comprises multiple strands, has been treated to be adhesive, has been treated to adhere to the pharmacologically acceptable carrier, or has been treated to adhere to the active agent, or has been treated to adhere to the active agent and pharmacologically acceptable carrier. In another aspect, the floss is treated to change its surface energy to facilitate in the deposition process, or to promote formation of uniform depositions. In another aspect, each adjacent deposition comprises a dye or indicia that distinguishes between adjacent deposition. In another aspect, the floss is not dipped into the active agent, the pharmacologically acceptable carrier, or both. In another aspect, the one or more active agents are selected from antigens, immunogens, allergens, or combinations thereof are not delivered to a vestibular mucosa. In another aspect, the one or more active agents trigger an immune response that is activating or anergizing an immune response by targeting a junctional epithelium in the gingival crevice. In another aspect, the floss has a thickness less than 5 mm, preferably less than 3 mm, and preferably less than 1 mm. In another aspect, the floss comprises natural or synthetic polymers, organic materials, metals, inorganic materials or combinations thereof. In another aspect, the floss comprises a mucoadhesive layer or a hydrophobic layer or a hydrophilic layer or a combination. In another aspect, the floss comprises a microporous structure allowing diffusion of antigen to gingival crevice. In another aspect, the one or more active agents comprise an amount of antigens, immunogens, allergens, or combinations thereof delivered to the junctional epithelium ranges from picograms to milligrams. In another aspect, the one or more active agents comprise antigens, immunogens, allergens, or combinations thereof desensitize an individual to the antigens, immunogens, allergens, or combinations thereof by 10%, 20%, 30%, 40%, 50%, 60%, 70%, 80%, 90% or 100%. In another aspect, the one or more active agents comprise antigens, immunogens, allergens, or combinations thereof desensitize the subject to the antigens, immunogens, allergens, or combinations thereof by between 0.1-100%. In another aspect, the floss delivers antigens, immunogens, allergens, or combinations thereof to the JE and the floss delivers antigens, immunogens, allergens, or combinations thereof to the JE is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more after the subject eats food, drinks water, or both. In another aspect, the one or more active agents activate, modify, or anergize an immune response. In another aspect, the one or more active agents trigger an immune response that targets at least one of: a bacteria, a virus, a fungi, a protozoan, a parasite, a prion, a toxin, a cancer, an allergy, or an auto-immune diseases. In another aspect, the one or more active agents comprise one or more antigens is selected from at least one of: proteins, peptides, deoxyribonucleic acid (DNA) oligonucleotides, ribonucleic acid (RNA) oligonucleotides, broken cells, intact cells, lipids, toxin variants, carbohydrates, virus-like particles, liposomes, live attenuated or killed natural or recombinant microorganisms, virosomes, polymeric/inorganic/organic micro and nanoparticles, or immune stimulating complexes (ISCOMS). In another aspect, the one or more active agents comprises an antigen that comprises a peptide obtained from a cancer cell or portion thereof selected from T- and B cell lymphoproliferative diseases, ovarian cancer, pancreatic cancer, head and neck cancer, squamous cell carcinoma, gastrointestinal cancer, breast cancer, prostate cancer or non-small cell lung cancer. In another aspect, the one or more active agents comprises an antigen that is a food allergen selected from peanut, shellfish, egg protein, milk protein, legumes, nuts, or an airway allergen selected from a house dust mite or pollen. In another aspect, the one or more active agents comprises an antigen that is at least one of attached, adsorbed, or anchored physically or chemically to a dental floss or thin device or to a strip/patch or an interdental brush with thickness suitable for its placement into the gingival crevice. In another aspect, the floss further comprises one or more adjuvants selected from a cytokine, chemokine, toll-like receptor ligands or activators, alum, muramyl dipeptides, pyridine, chitosan, saponins, oils, emulsions, bacterial cell wall extracts, bacterial proteins, cytoplasmic bacterial DNA or mimics, viral RNA or mimics, synthetic oligonucleotides, stimulator of interferon (IFN) genes (STING) agonists (2'3'-CGAMP, c-di-AMP, 2'3'-c-di-AM(PS)2 (Rp,RP), c-di-GMP, CL401, CL413, CL429, Flagellin, Imiquimod, LPS-EB, MPLA, ODN 1585, ODN 1826, ODN2006, ODN2395, pam3CSK 4, poly(I:C), R848, TDB), natural polymer (poly-γ-glutamic acid, chitosan, mannan, lipomannan, lentinan, dextran), synthetic polymer (poly-N-isopropylacrylamide, copolymers, block polymers, polyphosphazenes, polyelectrolytes, polyanhydrides, polymethacrylates, polyglycolic-co-lactide, polycaprolactones, polyvinylpyrrolidone, cationic polymers) and combinations thereof. In another aspect, the one or more active agents comprises one or more antigens, immunogens, allergens, or combinations thereof activate an innate immune response, an adaptive immune response, or both.

As embodied and broadly described herein, an aspect of the present disclosure relates to a method of making a floss that comprises a pre-determined amount of one or more active agents comprising: a floss; and a deposition on the floss in a discontinuous manner of one or more deposition of the active agent in a pharmacologically acceptable carrier, wherein each deposition has a known, pre-determined amount of the active agent. In one aspect, each adjacent deposition comprises the same active agent or a different active agent, or each adjacent deposition comprises the same active agent in a different concentration; or wherein each adjacent deposition comprises a different active agent in a different concentration; or each adjacent deposition h is placed on a different plane from the adjacent deposition; or each adjacent deposition is placed on an opposite side of the floss from the adjacent deposition; or adjacent depositions each comprise a different active agent from a prior adjacent deposition. In another aspect, the floss is solid, frayed, comprises multiple strands, has been treated to be adhesive, has been treated to adhere to the pharmacologically acceptable carrier, or has been treated to adhere to the active agent. In another aspect, each adjacent drop or patch comprises a dye or indicia that distinguishes between adjacent deposition s. In another aspect, the floss is not dipped into the active agent, the pharmacologically acceptable carrier, or both. In another aspect, the one or more active agents are selected from antigens, immunogens, allergens, or combinations thereof that are not delivered to a vestibular mucosa. In another aspect, the one or more active agents trigger an immune response that is activating or anergizing an immune response by targeting a junctional epithelium in the gingival crevice. In another aspect, the floss has a thickness less than 5 mm, preferably less than 3 mm, and preferably less than 1 mm. In another aspect, the floss comprises natural or synthetic polymers, organic materials, metals, inorganic materials or combinations thereof. In another aspect, the floss comprises a mucoadhesive layer or a hydrophobic layer or a hydrophilic layer or a combination. In another aspect, the floss comprises a microporous structure allowing diffusion of antigen to gingival crevice. In another aspect, the one or more active agents comprise an amount of antigens, immunogens, allergens, or combinations thereof delivered to the junctional epithelium ranges from picograms to milligrams. In another aspect, the one or more active agents comprise antigens, immunogens, allergens, or combinations thereof desensitize an individual to the antigens, immunogens, allergens, or combinations thereof by 10%, 20%, 30%, 40%, 50%, 60%, 70%, 80%, 90% or 100%. In another aspect, the one or more active agents comprise antigens, immunogens, allergens, or combinations thereof desensitize the subject to the antigens, immunogens, allergens, or combinations thereof by between 0.1-100%. In another aspect, the floss delivers antigens, immunogens, allergens, or combinations thereof to the JE is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more before the subject eats food, drinks water, or both. In another aspect, the floss deposit delivers antigens, immunogens, allergens, or combinations thereof to the JE is 0 hr, 0.1 hr, 0.2 hr, 0.3 hr, 0.4 hr, 0.5 hr, 0.6 hr, 0.7 hr, 0.8 hr, 0.9 hr, 1 hr, 2 hr, 3 hr, 4 hr, 5 hr, 6 hr, 7 hr, 8 hr or more after the subject eats food, drinks water, or both. In another aspect, the one or more active agents activate, modify, or anergize an immune response. In another aspect, the one or more active agents trigger an immune response that targets at least one of: a bacteria, a virus, a fungi, a protozoan, a parasite, a prion, a toxin, a cancer, an allergy, or an auto-immune diseases. In another aspect, the one or more active agents comprise one or more antigens is selected from at least one of: proteins, peptides, deoxyribonucleic acid (DNA) oligonucleotides, ribonucleic acid (RNA) oligonucleotides, broken cells, intact cells, lipids, toxin variants, carbohydrates, virus-like particles, liposomes, live attenuated or killed natural or recombinant microorganisms, virosomes, polymeric/inorganic/organic micro and nanoparticles, or immune stimulating complexes (ISCOMS). In another aspect, the one or more active agents comprises an antigen that comprises a peptide obtained from a cancer cell or portion thereof selected from T- and B cell lymphoproliferative diseases, ovarian cancer, pancreatic cancer, head and neck cancer, squamous cell carcinoma, gastrointestinal cancer, breast cancer, prostate cancer or non-small cell lung cancer. In another aspect, the one or more active agents comprises an antigen that is a food allergen selected from peanut, shellfish, egg protein, milk protein, legumes, nuts, or an airway allergen selected from a house dust mite or pollen. In another aspect, the one or more active agents comprises an antigen that is at least one of attached, adsorbed, or anchored physically or chemically to a dental floss or thin device or to a strip/patch or an interdental brush with thickness suitable for its placement into the gingival crevice. In another aspect, the floss further comprises one or more adjuvants selected from a cytokine, chemokine, toll-like receptor ligands or activators, alum, muramyl dipeptides, pyridine, chitosan, saponins, oils, emulsions, bacterial cell wall extracts, bacterial proteins, cytoplasmic bacterial DNA or mimics, viral RNA or mimics, synthetic oligonucleotides, stimulator of interferon (IFN) genes (STING) agonists (2'3'-cGAMP, c-di-AMP, 2'3'-c-di-AM(PS)2 (Rp,RP), c-di-GMP, CL401, CL413, CL429, Flagellin, Imiquimod, LPS-EB, MPLA, ODN 1585, ODN 1826, ODN2006, ODN2395, pam3CSK 4, poly(I:C), R848, TDB), natural polymer (poly-γ-glutamic acid, chitosan, mannan, lipomannan, lentinan, dextran), synthetic polymer (poly-N-isopropylacrylamide, copolymers, block polymers, polyphosphazenes, polyelectrolytes, polyanhydrides, polymethacrylates, polyglycolic-co-lactide, polycaprolactones, polyvinylpyrrolidone, cationic polymers) and combinations thereof. In another aspect, the one or more active agents comprises one or more antigens, immunogens, allergens, or combinations thereof activate an innate immune response, an adaptive immune response, or both.

BRIEF DESCRIPTION OF THE DRAWINGS

For a more complete understanding of the features and advantages of the present invention, reference is now made to the detailed description of the invention along with the accompanying figures and in which:

(FIG. 1A) Human mouth. (FIG. 1B) Structure of gingival crevice and junctional epithelium (JE). (FIG. 1C) Delivery of active agent to junctional epithelium in gingival crevice and the diffusion of active agent in junctional epithelium and adjacent tissue over time, (FIG. 1D) delivery of antigen molecule coated on floss and effect of flossing on mouse gum tissue, and (FIG. 1E) diffusion of ovalbumin (Ova) conjugated to rhodamine in gum tissue (ex-vivo). Flossing is performed, on each of the incisor tooth, by placing antigen deposited floss around the tooth and flossing for approximately ten to fifteen times so that the coated antigen gets deposited on the gum line. (FIG. 1F) Delivery efficiency of floss coated with fluorescein isothiocyanate (FITC) conjugated ovalbumin (Ova).

(FIG. 2A)(1) Coated floss stereomicrograph and FIG. 2A(2) flossing procedure in mice. (FIG. 2B) Vaccination schedule: Balb/c mice (n=5) were vaccinated by flossing antigen (Ovalbumin (Ova), a model antigen) deposited floss on their gums. Floss included a deposit of 25 μg Ova+/−25 μg CpG (single-stranded oligodeoxynucleotide adjuvant) and mice were vaccinated weekly, up to 4 weeks total. Mice treated with floss without any coating were treated as control. Systemic immune response: Mice were bled at day 28 and 56, and anti-Ova antibody response (at either 1:12500 or 1:2500 dilution) in serum was analyzed through enzyme-linked immunosorbent assay (ELISA). FIG. 2(C)(1)-(3) Anti-Ova antibody response at day 56-FIG. 2(C) (1) IgG, FIG. 2(C)(2) IgG1 and FIG. 2(C)(3) IgG2a. Individual mouse serum was used in analysis. FIG. 2(D)(1)-(3) shows the memory immune response: Vaccinated mice were euthanized, and bone marrow cells were collected. Cells were cultured in triplicates in a concentration of $1\times10^6$ cells per well with RPMI medium supplemented with 10% fetal bovine serum and penicillin-streptomycin antibiotics. Supernatant of cultured cells were collected post 96 h and anti-Ova responses were analyzed. FIG. 2(D)(1)-(3) Anti-Ova antibody response in bone marrow cells-FIG. 2(D)(1) IgG, FIG. 2(D)(2) IgG1, FIG. 2(D)(3) IgG2a. This result suggests that the response is not just local and systemic but was able to induce a memory response to better prepare individual for future exposure to same antigen (Ag). FIG. 2(E)(1)-(4) show the mucosal immune response. At day 56, fecal matter, nasal wash and lung lavage were collected from the vaccinated and mice that were treated with floss only. Anti-Ova FIG. 2(E)(1) IgG in fecal matter (1:5 dilution), FIG. 2(E)(2) IgA in fecal matter (1:5 dilution), FIG. 2(E)(3) IgG in nasal wash (undiluted), and FIG. 2(E)(4) IgG lung lavage (undiluted). FIG. 2(F)(1)-(2) No significant amount of IgE was detected either (1) in the serum or (2) in the bone marrow of the mice vaccinated through floss indicating that the target site of JE does not sensitize the individual against the delivered Ag. FIG. 2(G) Vaccinated mice were euthanized and splenocyte cells were collected. Cells were cultured, re-stimulated by Ova (200 μg/ml) in triplicates in a concentration of $1\times10^6$ cells per well with RPMI medium supplemented with 10% fetal bovine serum and penicillin-streptomycin antibiotics. Supernatant of cultured cells were collected post 96 h and cytokine levels were analysed. FIG. 2(G) shows cytokine levels in splenocyte culture, FIG. 2(G)(1) IFN-gamma, and FIG. 2(G)(2) IL-4. Data represented as mean±SD. One-way ANOVA test was used to compare between the groups at different serum dilutions. *$p<0.05$, $p<0.01$, *$p<0.001$, and ****$p<0.0001$.

FIG. 3(A) Vaccination schedule: Balb/c mice (n=10) were vaccinated either with 10 μg or 25 μg of Inactivated (Inac.) virus coated on a floss for a total of three times-once on each of day 0, 14 and 28. At day 56, mice were bled and anti-Inac. virus immune response (at either 1:800 or 1:50 dilution) was analyzed through ELISA. FIG. 3(B)(1)-(3) Anti-Inac. virus FIG. 3(B)(1) IgG, FIG. 3(B)(2) IgG1, FIG. 3(B)(3) IgG2a antibody response in serum at day 56. Virus challenge: At d56, mice were challenged with $3\times LD_{50}$ (lethal dose 50%) of A/PR/8/34 (H1N1) influenza virus. Individual mice samples were used in analysis. Data represented as mean±SD. One-way ANOVA test was used to compare between the groups. *$p<0.05$, $p<0.01$, *$p<0.001$, and **$p<0.0001$. FIG. 3(C)(1)-(2) Mice were observed every day for change in the body weight and severity of infection. FIG. 3(C)(1) Percent change in body weight, FIG. 3(C)(2**) percent survival rate of vaccinated mice after infection. n=5 mice in each group.

FIG. 4(A)(1) Stereomicrograph of floss coated with M2e-AuNP+CpG containing 56 μg of AuNP's, 8.1 μg of M2e and 20 μg of CpG (1× dose) and FIG. 4(A)(2) flossing procedure in mice. FIG. 4(B) Vaccination schedule: Balb/c mice (n=10) were vaccinated by either flossing vaccine formulation [M2e-AuNP+CpG (MAC)] coated floss on their gums or by placing the vaccine formulation [M2e-AuNP+CpG (MAC)] under tongue [sublingual immunotherapy (SLIT)]. Vaccine formulation (MAC), either coated on floss or delivered through SLIT, consisted of 56 μg of AuNP's, 8.1 μg of M2e and 20 μg of CpG (single-stranded oligodeoxynucleotide adjuvant) and mice were vaccinated on day 0 and day 21. Naïve mice that received no treatment were treated as control. Systemic immune response: Mice were bled at day 21 and 42, and anti-M2e antibody response (at 1:6400 dilution) in serum was analyzed through enzyme-linked immunosorbent assay (ELISA). FIG. 4C(1)-(3) Anti-M2e antibody response in serum at day 42-FIG. 4C(1) IgG, FIG. 4C(2) IgG1 and FIG. 4C(3) IgG2a. Individual mouse serum was used in analysis. Data represented as mean±SD. One-way ANOVA test was used to compare between the groups. *p<0.05, p<0.01, *p<0.001, and ****p<0.0001. Virus challenge. (FIG. 4D(1)-(2)) At day 43, mice were challenged with 3×$LD_{50}$ (lethal dose 50%) of A/California/07/2009 H1N1 virus. Mice were observed every day for change in the body weight and severity of infection. FIG. 4D(1) Percent change in body weight, FIG. 4D(2) percent survival rate of vaccinated mice after infection. n=5 mice in each group.

(FIG. 5A) Vaccination schedule: Balb/c mice (n=5) were vaccinated by flossing antigen (Peanut extract (PE)) deposited floss on their gums. Floss was deposited with 25 μg PE+/−25 μg CpG (single-stranded oligodeoxynucleotide adjuvant) and mice were vaccinated weekly, up to 4 weeks total. Mice treated with floss without any coating or deposits were treated as control. Systemic immune response: Mice were bled at day 28 and 56, and anti-PE antibody response (at 1:12500 dilution) in serum was analyzed through enzyme-linked immunosorbent assay (ELISA). FIG. 5B(1)-(3) Anti-PE antibody response in serum at day 56—FIG. 5B(1) IgG, FIG. 5B(2) IgG1 and FIG. 5B(3) IgG2a. Individual mouse serum was used in analysis. (FIG. 5C(1)-(3)) Memory Immune response: Vaccinated mice were euthanized, and bone marrow cells were collected. Cells were cultured in triplicates in a concentration of 1×$10^6$ cells per well with RPMI medium supplemented with 10% fetal bovine serum and penicillin-streptomycin antibiotics. Supernatant of cultured cells were collected post 96 h and anti-PE responses were analyzed. Anti-PE FIG. 5C(1) IgG, FIG. 5C(2) IgG1, FIG. 5C(3) IgG2a. This result suggests that the response is not just local and systemic but was able to induce a memory response to better prepare individual for future exposure to same antigen (Ag). (FIG. 5D) Mucosal immune response. At day 56, fecal matter, nasal wash and lung lavage were collected from the vaccinated and naïve mice. Anti-PE FIG. 5D(1) IgG in fecal matter (1:5 dilution), FIG. 5D(2) IgA in fecal matter (1:5 dilution), FIG. 5D(3) IgG in nasal wash (undiluted), and FIG. 5D(4) IgG lung lavage (undiluted). (FIG. 5E(1)-(2)) No significant amount of IgE was detected either FIG. 5E(1) in the serum or FIG. 5E(2) in the bone marrow of the mice vaccinated through floss indicating that the target site, junctional epithelium, does not sensitize the individual against the delivered Ag. (Data represented as mean±SD. One-way ANOVA test was used to compare between the groups at different serum dilutions. *p<0.05, p<0.01, *p<0.001, and ****p<0.0001.

(FIG. 6A) Immunotherapeutic schedule: Balb/c mice (n=5) were sensitized through oral route [1 mg peanut extract (PE)+15 μg cholera toxin (CT)], given at intervals of a week for five consecutive weeks. Mice were then vaccinated by flossing antigen-coated floss. Floss was coated with 5 μg PE+/−5 μg CpG (single-stranded oligodeoxynucleotide adjuvant) and mice were vaccinated three times per week, up to 3 weeks total. Sensitized mice that did not receive any treatment were kept as control (untreated). Mice were bled at day 10 post-vaccination (PV). Mice were challenged eight weeks post-vaccination with PE allergen (500 μg) through intraperitoneal route (IP), were then euthanized and different tissues were collected. (FIG. 6B(1)-(3)) Anti-PE antibodies in serum (at 1:12500 dilution) were confirmed through enzyme-linked immunosorbent assay (ELISA). Anti-PE FIG. 6B(1) IgG, FIG. 6B(2) IgG1 and FIG. 6B(3) IgG2a antibody response at day 10 post-vaccination. Individual mouse serum was used in analysis. Data represented as mean±SD. One-way ANOVA test was used to compare between the groups at different serum dilutions. *p<0.05, p<0.01, *p<0.001, ****p<0.0001. and ns: not significant. PE induced anaphylaxis. (FIG. 6C) (1) Plasma MCPT-1 levels post IP challenge with PE. Histological analysis of intestinal tissue. (FIG. 6D) Eight weeks post-vaccination, mice were challenged with PE allergen (500 μg) through intraperitoneal route. Mice were then euthanized, and small intestine was collected from proximal, middle and distal ends, fixed, dehydrated and embedded in paraffin wax for cutting. Tissue sections were stained with hematoxylin and eosin (H & E) stain and sectioned for histology. FIG. 6D(1) Number of eosinophils counted in respective sections from mice of different treatment groups. FIG. 6D(2) Bright-field image of H & E stained intestine with arrows pointing to eosinophil infiltration. Individual mouse sample was used in analysis. Data represented as mean±SD. One-way ANOVA was used to compare between the groups. *p<0.05, p<0.01, *p<0.001 and ns: not significant.

FIGS. 7A to 7D show airway allergen immunotherapy. (FIG. 7A) Immunotherapeutic schedule: Balb/c mice (n=5) were sensitized through two intraperitoneal (IP) injection (25 μg Ova+2 mg of alum (an adjuvant)), given at interval of a week. Ten days post sensitization (PS), mice were challenged with Ova (50 μg) through intranasal route (IN) for three consecutive days to develop airway inflammation. Mice were then vaccinated by flossing with floss onto which antigen was deposited. Floss was coated with 25 μg Ova+/−25 μg CpG (single-stranded oligodeoxynucleotide adjuvant) and mice were vaccinated three times per week, up to 3 weeks total. Sensitized mice that did not receive any treatment were kept as control (untreated). Mice were bled at day 10 post-vaccination. Mice were challenged on day 28 post-vaccination with Ova allergen (50 μg) through intranasal route (IN) for three consecutive days, were then euthanized and different tissues were collected Systemic immune response: (FIG. 7B(1)-(4)) Anti-Ova FIG. 7B(1) IgG, FIG. 7B(2) IgG1, FIG. 7B(3) IgG2a and FIG. 7B(4) IgE antibody response in serum (at either 1:12500 or 1:500 or 1:20 dilution) at day 10 post-vaccination analyzed through enzyme-linked immunosorbent assay (ELISA). (FIG. 7C) Lung lavage analysis post-challenge. Mice were then euthanized, and mucosal secretion of lung lavage was collected. Cell count of FIG. 7C(1) eosinophils and FIG. 7C(2) neutrophils in lung lavage-cells were stained with diff-stain kit and counted by observing cells under confocal microscope. Histological analysis of lungs: (FIG. 7D) Mice were then euthanized, and lungs were harvested, fixed, cleaned and sectioned for histology. Tissue sections were stained with either periodic acid-Schiff (PAS) to stain for mucus deposition or trichrome blue (TCB) to stain for collagen deposition. Representative brightfield image of PAS stained lung (top panel) and TCB stained lung (bottom panel). Arrows in the top panel point to mucus deposition, and to collagen deposition in the bottom panel.

DETAILED DESCRIPTION OF THE INVENTION

Figure 1A:
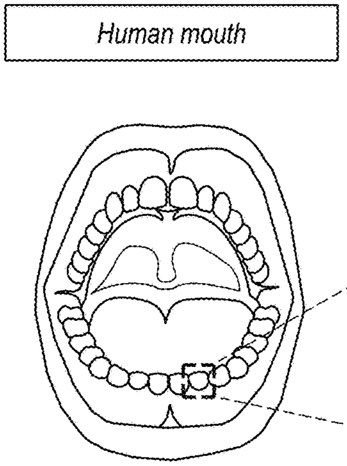
FIGS. 1A to 1F show the gingival crevice and junctional epithelium.
Figure 1B:
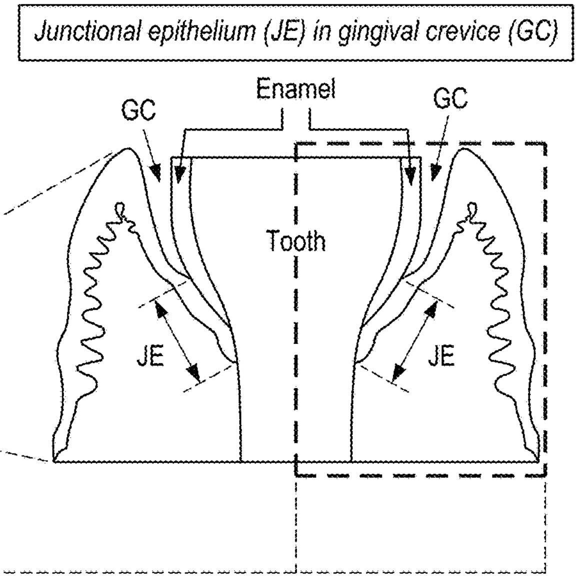
Figure 1C:
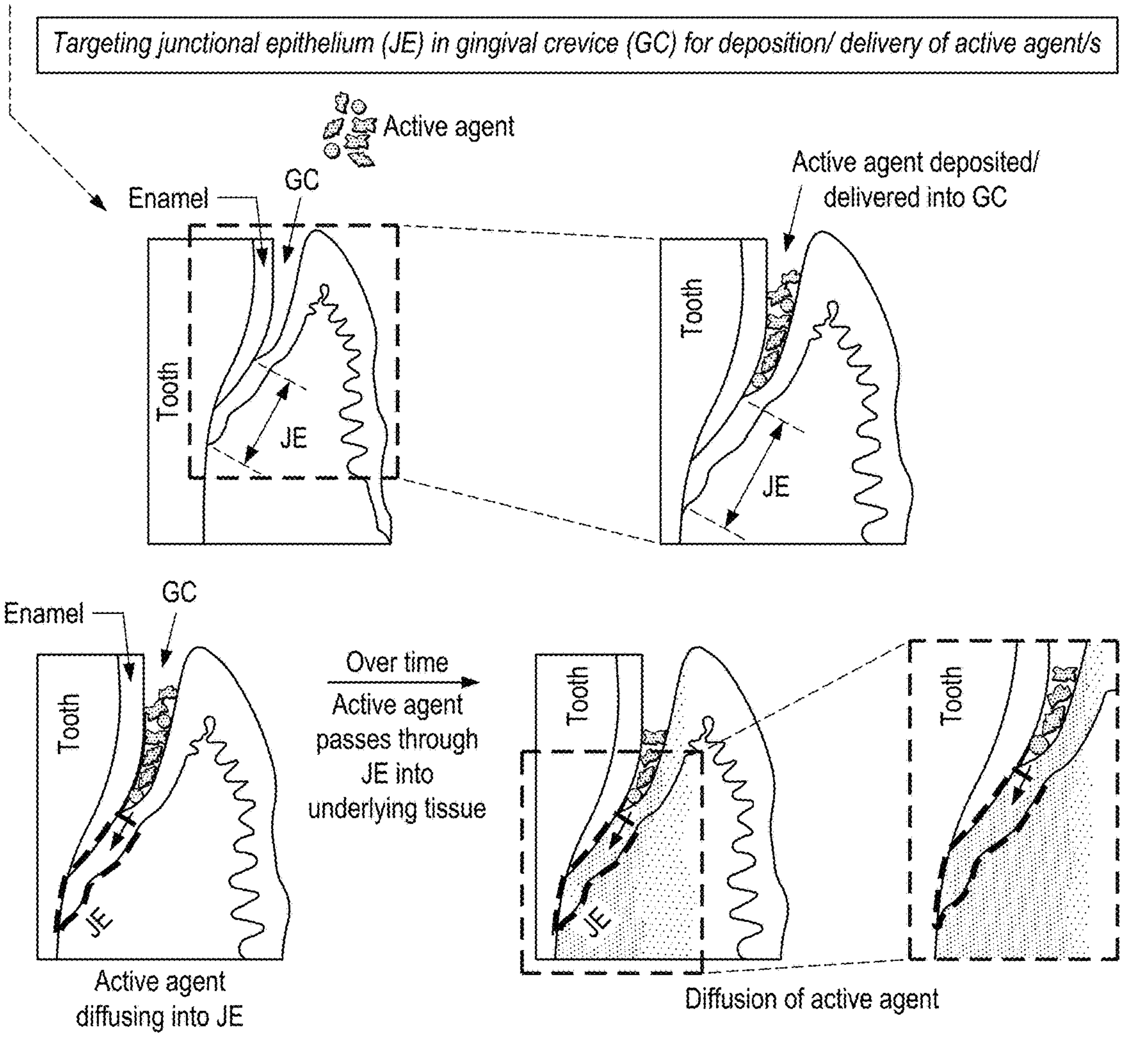
Figure 1D:
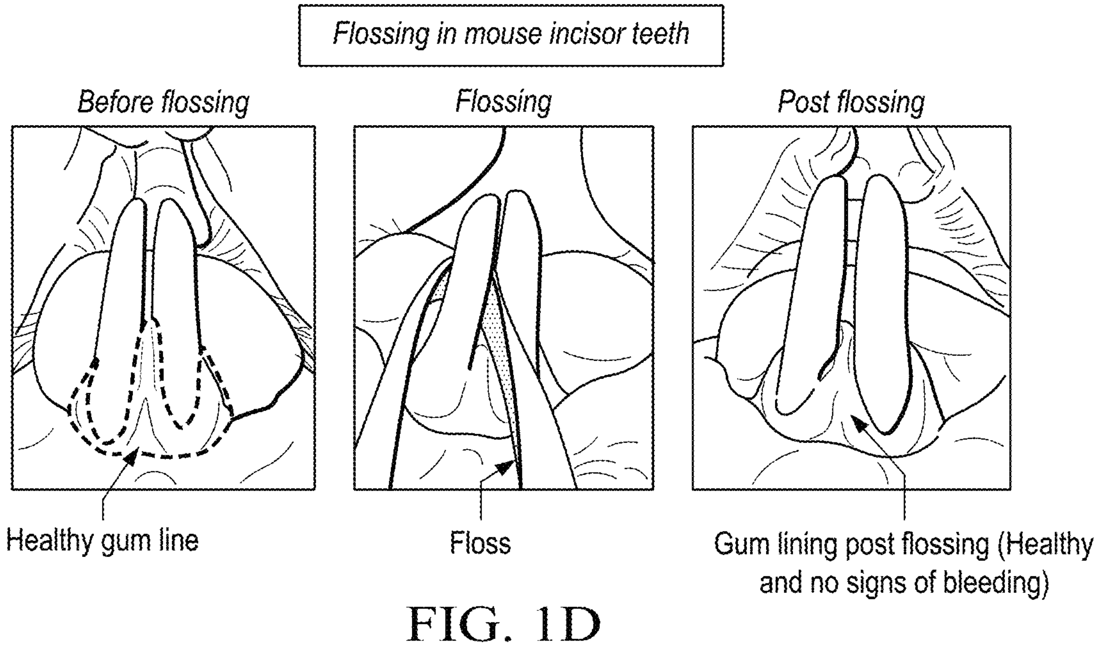
Figure 1E:
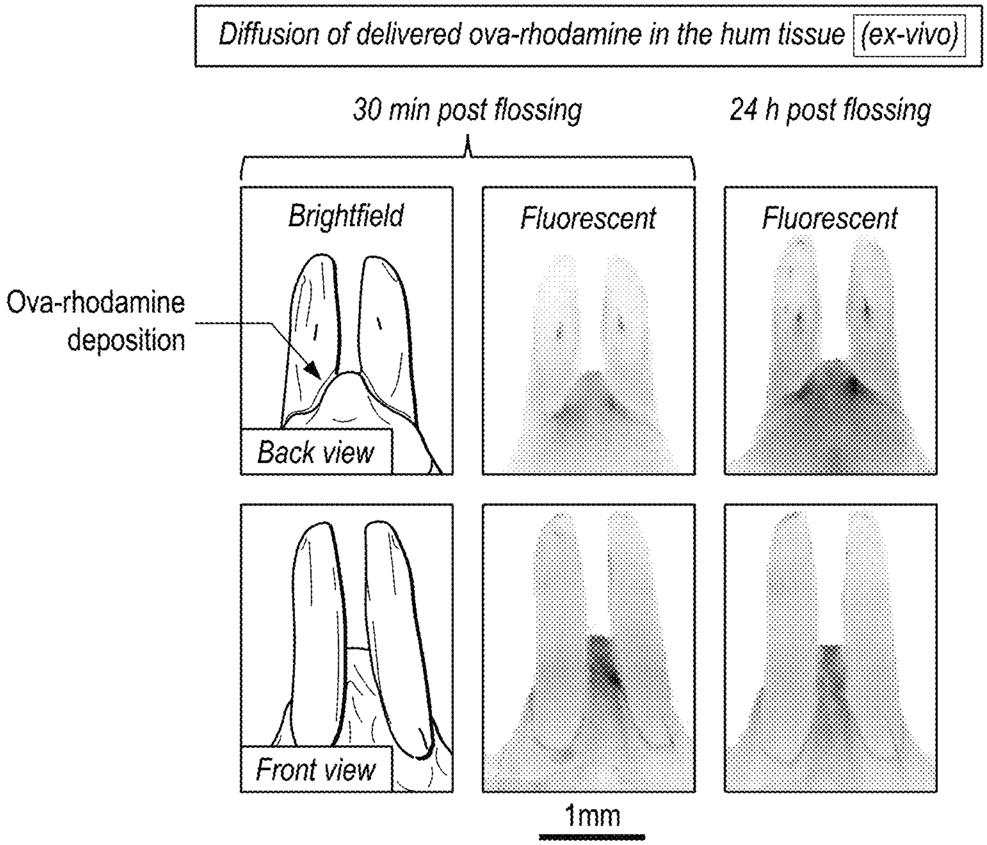
Figure 1F:
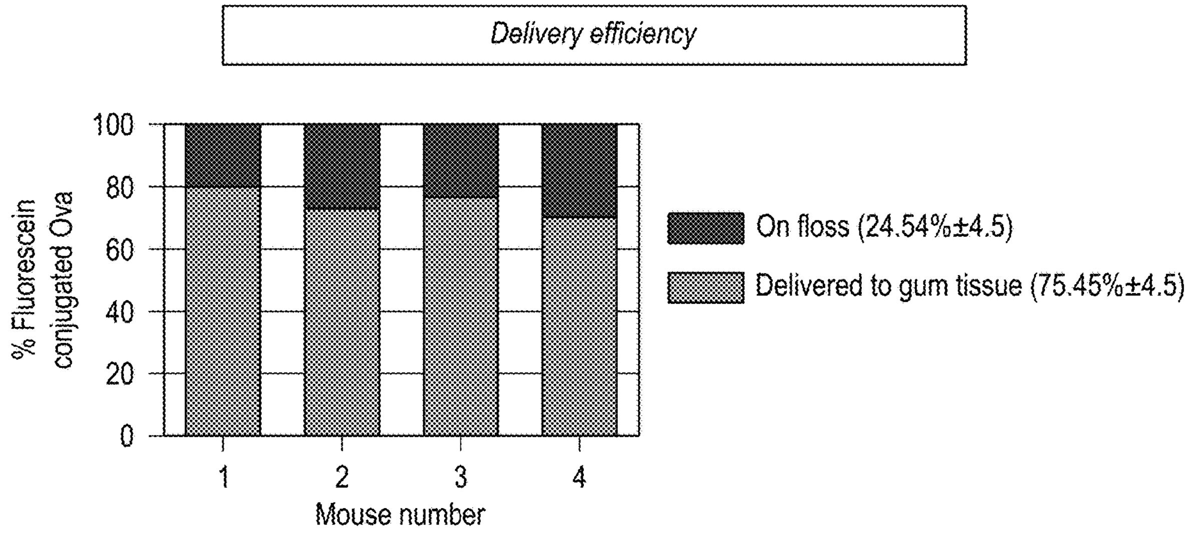

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as “a”, “an” and “the” are not intended to refer to only a singular entity, but include the general class of which a specific example may be used for illustration. The terminology herein is used to describe specific embodiments of the invention, but their usage does not delimit the invention, except as outlined in the claims.

U.S. Pat. No. 9,271,899 (the ’899 patent) entitled “Methods, Articles And Kits For Allergic Desensitization, Via The Oral Mucosa,” claims to perform allergic immunotherapy on individuals by targeting oral mucosa with regions of high dendritic cells to mast cells ratio, especially vestibular mucosa. Specifically, the first paragraph of the description of the invention states, “The invention relates to allergic immunotherapy targeting regions of the oral mucosa, such as those having a high dendritic to mast cell ratio, in particular targeting the vestibular mucosa.” The oral vestibule is a narrow slit-like portion of the mouth that is bounded on the inside by the gums and teeth, and on the outside by the cheeks and lips. Although the patent focuses particularly on vestibular mucosa it mentions that allergen could be in contact with other oral mucosal sites such as gingival/buccal. The ’899 patent argues for the need to provide methods for enhancing delivery of allergens to the sections of oral mucosa, with desired dendritic to mast cell ratio, specifically, a high dendritic to mast cell ratio, and that maximize the contact time between an allergen and vestibular tissue of oral cavity. The methods of delivery of allergen includes toothpaste, pouch, dental cream, mouth wash, mouth, spray, etc. The ’899 patent discusses formulations that includes between 1 picogram to 15 mg allergen proteins that can be given through a pouch or other dental product. The ’899 patent discusses about making a formulation in form of a toothpaste that includes an allergen. It states an example where a 2 gm of toothpaste can include 1 to 10% of the allergen. Thus, an individual would be receiving 2-200 mg of allergen according to this method. On the one hand, the ’899 patent makes the argument that high dendritic to mast cell ratio is important, and proposes that the vestibular mucosa is one such mucosa of interest, yet the methods described in the ’899 patent do not teach how these mucosa, and specifically the vestibular mucosa are predominantly targeted, and is also silent on any dose that reaches cells in vestibular tissue.

In contrast, the technology of the present invention specifically targets junctional epithelium (JE), to deliver picograms to micrograms of allergen/vaccine molecules to the JE, to generate an immune response. The JE is located at the very bottom in the deepest recess of the gingival crevice (also sometimes called gingival sulcus or gingival groove or gum pocket). The JE is not freely exposed, instead, on its one side the JE is attached to the hard tooth surface, and on the other side it is attached to the soft underlying connective tissue. In this manner, JE wraps around the tooth forming an attachment band. The cells in JE are non-keratinized and have wide intercellular spaces. This wide intercellular spacing in JE, confers a unique property of high permeability to JE that is not found elsewhere in the oral mucosa including the mucosa of cheeks, lips, attached gingiva and even the vestibule. This high degree of permeability of JE is even higher than sublingual mucosa, which at the moment is considered to be the most permeable oral mucosal site. The inventors of this invention have recognized this uniqueness of JE, and have shown herein that microgram quantities of antigenic molecule were able to readily permeate through the JE and induce a robust immune response in mice. As such, the technology of the present invention targets the J E because it has high permeability and allows for efficient uptake of the molecules into the underlying tissue, which help to generate a strong immune response. The present invention also directly compares junctional targeting of immunogens (vaccine/allergen) to sublingual immunotherapy (SLIT) and demonstrates significantly higher immune response by targeting the junctional epithelium when compared to SLIT. In contrast, the ’899 patent does not focus on permeability, and in fact the permeability of vestibular mucosa, is less than that of JE. The ’899 patent further discusses about use of floss to deliver allergen. It states that the allergen can be embedded into coating layer or allergen can be directly coated on floss as a coating layer. The allergen then desorbs or gets released from the floss to deliver antigenic material to the vestibular mucosa. But it does not mention where does the allergen, delivered with a floss, gets delivered to. Additionally, the ’899 patent does not teach about junctional epithelium nor its uniquely high permeability, nor does the ’899 patent talk about vaccination. In contrast, the present invention targets the junctional epithelium in the gingival crevice, namely, areas with a lower dendritic cell population than the vestibular mucosa, which is contrary to the teaching of the '899 patent. It is documented that the dendritic cell population in human oral mucosa are lower in number in gingiva as compared to vestibulum, buccal, palate, and lingual tissues. In fact, the highest numbers of LCs were found in the vestibulum, buccal, palate, and lingual tissues, while lower numbers were observed in the sublingual area and gingiva (Reference: "Dendritic cells of the oral mucosa", A-H Hovav, Mucosal Immunology, 7, 27-37, 2014). The reference article, Allam et al. Allergy 2008: 63:720-727, from '899 patent, which forms the basis of the patent's teachings, also confirms that gingiva has the highest number of mast cells, and therefore, as per the '899 patent teachings, the junctional epithelium should be less preferred/favored for allergen immunotherapy. Furthermore, the present invention is not targeted to the vestibular mucosa.

The oral cavity mucosa in this present invention, contrary to the dogma that simply placing molecules on a mucosal surface does not lead to efficient immune modulation, it is demonstrated that in fact if material is placed on top of the junctional epithelium, a strong immune modulatory response can be achieved. No additional approaches are required to weaken or disrupt the mucosal barrier at the junctional epithelium, simply placing small molecules such as deoxyribonucleic acid (DNA), or large molecules such as proteins, and even nanoparticles and viruses on the junctional epithelium can result in strong immune responses. In fact, the junctional epithelium is rich in lymphatic vessels.

The present invention is directed to administering antigens and allergens through the junctional epithelium in the gingival crevice in order to access strong systemic and mucosal immune responses. Because the junctional epithelium is only 2 mm long and the gingival crevice is 1-2 mm deep, the inventors deposited onto dental floss an antigen and/or an allergen for targeted deposition into the gingival crevice for uptake through the junctional epithelium. While the inventors used a floss to target the junctional epithelium, other approaches that can target the junctional epithelium could be used. For example, a thin flat surface similar in dimensions to the gingival crevice could be used. This flat surface could either be coated with the material of interest to cause immunomodulation, or the material could be encapsulated in the flat surface. The inventors show, using mouse models, that floss can be coated with the antigen/allergen solution, show that the mice teeth can be flossed, and show that this method is as an effective form of antigen/allergen delivery. This new approach serves as a non-invasive, painless, and easy way to administer allergens and antigens for immune modulation. In the case of allergies, the immunization of the present invention serves to dampen the allergic immune response and/or induce a protective immune response against allergen/s. Conversely, the present invention can also be used to trigger an immune response against infectious and other agents.

The present invention can be used with dental floss that is well known in the art. For example, dental floss may be produced as a nylon dental floss in which a nylon is polymerized into a polymer that is formed, pumped, or extruded to form monofilaments or a multitude of filaments. The polymer is allowed to harden, and the monofilaments or a multitude of filaments is combined to form a strand or strands of dental floss. Dental floss may be produced from polytetrafluoroethylene (PTFE or TEFLON®), polypropylene, polyethylene, styrene butadyene copolymers, of combinations thereof. Once formed, the polymer can be melted and extruded into thin strands. See e.g., U.S. Pat. No. 6,270,890, relevant portions incorporated herein by reference.

In one non-limiting example, nylon or PTFE is mixed with a basic amino acid (or a salt thereof), and formed or extruded to form one or more filaments. In the case of multiple filaments, these are generally twisted to form the dental floss. Alternatively, a single ribbon of floss, such as PTFE, can be formed. Often, the dental floss will have a denier of about 450 to about 1350, and in other examples, a floss dernier is from about 100 to about 900.

The dental floss is then deposited with the immunogen(s) and/or allergen(s) and/or antigen(s) of the present invention, as will be known to the skilled artisan. For example, the dental floss is treated in a bath comprising the antigen and/or allergen. The bath may include one or more waxes that adhere to the floss, and thereby cause the antigen and/or allergen to adhere to the floss. In one example, a dental floss comprising a nylon or a PTFE fiber is coated with the antigen and/or allergen. A wax or polymer, e.g., such as polyvinyl alcohol, polyvinyl acetate, can be used to coat the antigen and/or allergen in, or, or about the dental floss. See e.g., U.S. Pat. No. 6,289,904, relevant portions incorporated herein by reference.

For a filamentous dental floss, the antigen and/or allergen can be embedded into the bundle of thin filaments, e.g., nylon filaments, prior to the bundles being formed, while the bundles are formed, or even after they are formed. The bundles may then also be, optionally, coated with a wax or polymer. The number of filaments can be from about 2 to about 500, e.g., from about 2 to about 250, depending on the denier of the dental floss filaments. The dental floss filaments are often twisted with about 1 to 5 twists per inch to form the floss. The twisting provides integrity to the dental floss when placed on a spool and/or during subsequent handling. For immunization, the dental floss filaments will spread out and splay against tooth surfaces at the junctional epithelium of the gingiva, thereby delivering the antigen and/or allergen immunization. The floss may also be formed of interlocking fibers. The dental floss product will preferably of a thickness that allows it to fit not only between the teeth, but to reach the junctional epithelium of the gingiva. Where multiple filaments are used, the coating may be applied before and/or after twisting and generally after application of the antigen and/or allergen. Other additives may be applied to the dental floss to preserve the antigen and/or allergen or to help in the coating process or to achieve controlled release of the antigen and/or allergen.

In addition, a flavor can be applied as a liquid or a solid to the dental floss. Flavors can be spray dried in liquid or solid form. When flavor is applied as a liquid, the floss is generally dried prior to being wound onto a spool. The drying can be air drying or drying until heat, after which the floss is wound onto a spool.

As used herein, the term "antigen" refers to a molecule that can initiate a humoral and/or cellular immune response in a recipient of the antigen. Antigen may be used in different contexts with the present invention, for example, but not limited to: (1) as an agent to generate an immune response to prevent or treat a disease or condition for which a vaccination would be advantageous treatment, and/or (2) as an agent that anergizes an immune response, that is, it causes immune cells that have been activated to reduce their level of activation, and/or (3) as an agent to modulate the immune response to achieve a beneficial therapeutic effect in the subject. Antigens include any type of biologic molecule, including, for example, simple intermediary metabolites, sugars, lipids and hormones as well as macromolecules such as peptides, polypeptides, complex carbohydrates, phospholipids, nucleic acids and/or glycoproteins or combinations thereof. Common categories of antigens include, but are not limited to, viral antigens, bacterial antigens, fungal antigens, protozoal and other parasitic antigens, tumor antigens, and conversely, antigens involved in autoimmune disease, allergy and graft rejection, and other miscellaneous antigens.

Examples of viral antigens disclosed herein include, e.g., retroviral antigens such as retroviral antigens from the human immunodeficiency virus (HIV) antigens such as gene products of the gag, pol, and env genes, the Nef protein, reverse transcriptase, and other HIV components; coronavirus antigens such as spike protein, nucleoprotein, messenger RNA (mRNA); hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components, west nile virus; yellow fever; tularemia; hepatitis (viral; bacterial); RSV (respiratory syncytial virus); HPIV 1 and HPIV 3; adenovirus; small pox See Fundamental Virology, Second Edition, eds. Fields, B. N. and Knipe, D. M. (Raven Press, New York, 1991) for additional examples of viral antigens, relevant portions incorporated herein by reference.

Other examples of antigens include whole, heat-killed, or portions, thereof, including picornavirus, coronavirus, togavirus, flavivirus, rhabdovirus, paramyxovirus, orthomyxovirus, bunyavirus, arenavirus, reovirus, retrovirus, papillomavirus, parvovirus, herpesvirus, poxvirus, hepadnavirus, spongiform virus, influenza, herpes simplex virus 1 and 2, measles, dengue, smallpox, polio or HIV. Other antigens may be against pathogens such as trypanosomes, tapeworms, roundworms, helminthes, malaria. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Examples of bacterial antigens disclosed herein include, e.g., bacterial antigens such as pertussis toxin, filamentous hemagglutinin, pertactin, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *Haemophilus* influenza bacterial antigens such as capsular polysaccharides and other *Haemophilus* influenza bacterial antigen components; anthrax bacterial antigens such as anthrax protective antigen and other anthrax bacterial antigen components; rickettsiae bacterial antigens such as rompA and other rickettsiae bacterial antigen component. A lso included with the bacterial antigens described herein are any other bacterial, mycobacterial, mycoplasmal, rickettsial, or chlamydial antigens, such as *Neisseria meningitidis; Streptococcus pneumoniae; Neisseria gonorrhoeae; Salmonella* serotype *typhi; Shigella; Vibrio cholerae*; Dengue Fever; Encephalitides; Japanese Encephalitis; lyme disease; *Yersinia pestis.*

Examples of fungal antigens for use with the present invention include, but are not limited to, e.g., *candida* fungal antigen components; *Histoplasma* fungal antigens such as heat shock protein 60 (HSP60) and other *Histoplasma* fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens for use with the present invention include, but are not limited to, e.g., *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasma antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

Examples of tumor antigens for use with the present invention include, but are not limited to, e.g., CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17 (gp 100), GnT-V intron V sequence (N-acetylglucosaminyltransferase V intron V sequence), Prostate Ca psm, PRAME (melanoma antigen), beta-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., CII, SLE or MG. In such diseases, it can be desirable to direct an ongoing antibody-mediated (i.e., a Th1/Th17-type) immune response to the relevant autoantigen towards a cellular (i.e., a Th2-type) immune response. Alternatively, it can be desirable to prevent onset of or decrease the level of a Th1/17 response to the autoantigen in a subject not having, but who is suspected of being susceptible to, the relevant autoimmune disease by prophylactically inducing a Th2 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., collagen type II protein/peptides, myelin oligodendrocyte glycoprotein (MOG), endogenous hormones such as luteinizing hormone, follicular stimulating hormone, testosterone, growth hormone, prolactin, and other hormones.

Example of antigens involved in autoimmune diseases, allergy, and graft rejection for use with the present invention include, but are not limited to, e.g., diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves opthalmopathy, sarcoidosis, primary biliary cirrhosis, uveitis posterior, and interstitial lung fibrosis. Examples of antigens involved in autoimmune disease include collagen type II, collagen type II peptide (CII250-270), proteoglycan, citrullinated peptide antigens, vimentin, fibrinogen, α-enolase, peptidyl arginine deiminase-4, insulin, islet antigen 2 (IA2), zinc transporter 8 (ZnT8), islet specific glucose-6-phosphatase catalytic subunit related protein (IGRP), chromogranin A (ChgA), islet amyloid polypeptide (IAPP), glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, insects derived antigens such as house dust mite (i.e, Der p1, Der p2, LTN-DP2-1, LTN-DPE-1), cockroach antigens (i.e., Bla g2), animal derived antigens such as feline antigens (i.e., Fel d1), dog antigens (i.e., Can f1), histocompatibility antigens, food allergens such as peanut antigens (Ar1 h1, Ara h2, Ara h3, Ara h6), milk antigens (i.e., Bos d11, Bos d4, Bos d6, Bos d8), egg protein (i.e., Gal d2, Gal d3, Gal d4), shrimp antigens (i.e., Tropomyosin), nuts (i.e., hazelnut Cor a 9, almond Pru du6), legumes (i.e., soybean Gly m6) and antibiotics such as penicillin, cephalosporins and other therapeutic drugs (such as insulin, epinephrine). Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease. The antigen can be crude or purified extract from the allergy-causing agent, such as extract from respiratory allergen (such as pollens, dust mite, insect and others), food allergens (such as peanut, cashew nut, walnut, soy, shellfish, and other), venom (such as bee venom) and other allergens.

As used herein, the terms "deposit," "depot", "deposition" refer to the placing in the form of one or more deposits of the active agent that are separated by a space from adjacent deposit(s) onto a floss.

As used herein, the term "epitope(s)" refer(s) to a peptide or protein antigen that includes a primary, secondary or tertiary structure similar to an epitope located within any of a number of pathogen polypeptides encoded by the pathogen DNA or RNA, and/or allergen that is immunogenic.

The antigen(s) and/or epitopes(s) are not limited to peptides, proteins and portions thereof, but can include genes, plasmids, vectors (viral, bacterial and non viral), DNA, RNA, CRISPR molecules, mRNA, siRNA, or other nucleotides either individually or in combination. Pharmaceutically acceptable carriers and formulations maybe used to stabilize these molecules or to enhance their function or to offer controlled release.

As used herein, the term "pharmaceutically acceptable carrier" refers to a carrier that does not cause an untoward effect in subjects (e.g., human being/s and pets (such as dog, cat, cows, pigs or other domesticated animals or even non-domesticated animals) to whom it is administered. Suitable pharmaceutically acceptable carriers include, for example, one or more of water, saline, phosphate buffered saline, dextrose, glycerol, ethanol, dimethyl sulfoxide, or the like and combinations thereof. In addition, if desired, the immunization/vaccine can contain minor amounts of auxiliary substances such as wetting or emulsifying agents, pH buffering agents, and/or adjuvants which enhance the effectiveness of the vaccine.

Non-limiting examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton in, e.g., a 2% squalene/Tween 80 emulsion. STING agonists (e.g., 2'3'-cGAMP, c-di-AMP, 2'3'-C-di-AM(PS)2 (Rp,RP), c-di-GMP, CL401, CL413, CL429, Flagellin, Imiquimod, LPS-EB, MPLA, ODN 1585, ODN 1826, ODN2006, ODN2395, ODN 1018, pam3CSK 4, poly(I:C), R848, TDB), Other examples of adjuvants include DDA (dimethyldioctadecylammonium bromide), Freund's complete, incomplete adjuvants, QuilA, natural polymer (i.e., poly-γ-glutamic acid, chitosan, mannan, lipomannan, lentinan, dextran), synthetic polymer (i.e, poly-N-isopropylacrylamide, copolymers, block polymers, polyphosphazenes, polyelectrolytes, polyanhydrides, polymethacrylates, polyglycolic-co-lactide, polycaprolactones, polyvinylpyrrolidone, cationic polymers). In addition, immune modulating substances such as lymphokines (e.g., IFN-gamma, IL-2 and IL-12) or synthetic IFN-gamma. inducers such as poly I:C can be used in combination with adjuvants described herein.

As used herein, the term "subject" refers to human being/s, pets (such as dog, cat, cows, sheep, goats, horses, rabbits, or pigs) or other domesticated animals, or non-domesticated animals such as deer, buffalo, or wild horses.

The junctional epithelium is located at the bottom of the gingival crevice, which is 1-2 mm deep in healthy gums. Furthermore, the apical tissue of the gingival cavity tightly hugs the teeth, allowing only thin instruments measuring less than 1 mm and preferably less than 500 μm to enter the cavity Thus, administration of material into the gingival crevice is not trivial. To overcome this challenge, the present invention uses an antigen and/or allergen deposited onto dental floss. The dental floss is used by millions of people daily to clean their gingival crevices, and this invention describes that it can be coated with the antigen/allergen for targeted deposition into the gingival crevice for uptake through the junctional epithelium. Dental floss offers additional benefits of being non-invasive, painless, and possible self-administration in the comfort of home. The dental floss should be taken as a non-limiting example of a system with the final goal of delivering material to the junctional epithelium. Other approaches based on the principle of enabling and allowing devices to enter the gingival crevice to help target the junctional epithelium such as tapes, films, strips, strings, threads, sutures, gels, hydrogels, polymers, viscous materials, particles or combinations thereof are included in this invention. These systems and devices maybe inserted into the gingival crevice, but may also be placed at the apical aspect of the gingival crevice rather than in to the crevice, and the molecule(s) of interest may then diffuse from the systems and devices into the gingival crevice and ultimately to junctional epithelium for permeation into the tissues. These systems that are placed on the apical side of the gingival crevice maybe designed such that they maximize diffusion of molecules into the gingival crevice, but minimize their loss outward and into the general oral cavity. In one such approach the delivery system can be coated with an impermeable layer on the side that faces opposite to the gingival crevice.

To coat the floss, the inventors developed a simple manual coating process of applying the material on the floss using a pipette. They selected Oral-B® Glide Pro-Health Original Floss from amongst five different flosses after preliminary coating feasibility studies. Using this method, the inventors were able to coat different molecules on the floss including proteins, small molecules, peptide, nanoparticles, single stranded DNA oligonucleotide and influenza virus. Next, the inventors established the feasibility of flossing teeth of mice. The inventors chose to floss the lower front incisor teeth due to ease of accessibility. Flossing was done by keeping the mouse under anesthesia. The figures show the incisors before, during and after flossing. Imaging under a fluorescent stereomicroscope confirmed that the coated fluorescent ovalbumin (Ova) gains entrance through junctional epithelium and into the gingival tissue in under 30 min. The inventors determined the fraction of Ova delivered into gingival crevice by quantifying Ova coated on floss (M1) and Ova left on floss after flossing (M2). For n=4 mice, the delivery efficiency ([M1−M2]/M1×100) was about 75%.

Immune response generated when antigen or allergen is administered to the junctional epithelium. The inventors coated Ova (25 μg Ova+/−25 μg CpG), peanut extract proteins (PE) (25 μg PE+/−25 μg CpG), or inactivated flu virus (A/PR/8/34 (H1N1)) (25/10 μg PR8) on the floss and administered 5 weekly doses for Ova and PE, and 3 bi-weekly doses for flu virus. Serum samples collected on day 56 (day 0 means day of first dose) clearly showed strong stimulation of systemic IgG responses towards Ova, PE, and PR8, and fecal matter analysis showed development of mucosal IgA and IgG. A clear adjuvant effect of CpG was seen, because responses, especially IgG2a, from use of CpG were significantly higher.

Determining if administration to junctional epithelium causes IgE production, which would show an allergic reaction. Serum IgE antibodies specific to Ova and PE were insignificant and comparable to mice receiving just floss (uncoated), suggesting that floss-based targeting of junctional epithelium does not induce allergies.

Flu vaccine administered at junctional epithelium is protective. Mice receiving inactivated PR8 as vaccine were challenged with 3×50% lethal dose. The figures show that mice were protected and exhibited minimal weight loss.

Using the present invention the effectiveness of floss with peanut extract (PE) or Ova for treatment of mice sensitized to peanut as food allergy model or Ova in an airway allergy model can be determined. For both allergy models, sublingual immunotherapy (SLIT) can be used as a positive control. Recently, FDA also approved a sublingual tablet for pollen allergy SLIT. SLIT requires a large amount of allergen to be placed under the tongue because permeability of this epithelium is not very high. For peanut immunotherapy, peanut sensitized mice received nine doses of 5 μg PE without CpG (Floss:PE) or with 5 μg CpG (Floss:PE+CpG) spread over 3 weeks. Two control groups were added: first group was of sensitized mice that received no treatment (Untreated), second was of naïve mice that received oral peanut challenge (Naïve mice with challenge only). Mice were challenged intraperitoneally with 500 μg of PE to assess treatment efficacy. As indicated by lower allergy-symptom clinical score, lower mast cell degranulation quantified through MCPT-1 marker, and lower infiltration of eosinophils in mouse intestinal tissue after challenge, floss provided superior desensitization over Untreated mice, and required fewer administrations (9) and lower doses. As expected, the peanut sensitized mice, which were untreated had significantly higher MCPT-1 and eosinophils in intestinal tissue. Naïve mice with challenge only had no abnormal readings after the challenge. Similarly, for Ova airway-allergy model, Ova sensitized mice received nine doses of 25 μg OVA without CpG (Floss:Ova) or with 25 μg CpG (Floss:Ova+CpG) in 3 weeks. A control group was added: sensitized mice that received no treatment (Untreated). Mice were challenged with three doses of 50 μg/day of Ova intranasally. The floss groups had lower inflammatory cells (eosinophils and neutrophils) and low mucus in lungs. The control untreated group showed significant inflammatory cells and mucus production. Mucus, which is a hallmark of airway allergic response was lower in the floss group, it suggests a better response at lower dose was stimulated.

To gain an insight into cellular responses, splenocytes of mice administered Ova were restimulated invitro with Ova (Note: These mice belonged to vaccination study and not the airway allergy). The cytokine profile showed that a both TH1 and TH2 effector response was being produced in mice receiving Ova+CpG. The bone marrow cells of these same mice without restimulation produced Ova-specific IgG and so did that of mice that received PE+CpG (vaccine study and not the foodway allergy). This shows that the response is systemic and not just local, and suggests generation of memory response, although more studies are required to confirm it.

These studies demonstrate that the floss can be coated, the coated floss can be used to target the junctional epithelium, which generates systemic and mucosal immune responses. The administration method also protected mice from lethal flu virus challenge and exhibited desensitization in airway allergy and peanut food allergy mouse models.

The inventors used a pipette tip to manually coat the floss using a solution containing the antigen/allergen. To increase reproducibility of coating and to increase delivery efficiency, an automated coating approach using computer-controlled linear stages and fluid dispensing systems can be used. A floss-coater can be used to coat a specific length of the floss with any antigen or allergen by simply switching out a coating liquid vial. Other options for coating include dip-coating, or spray coating, or ink jet printing, or pipette based coating, or cartridge printing or a combination thereof. The coating may require excipients such as thickening agents or surface tension reducing agents to improve coating and delivery efficiency. Additionally, to improve stability of molecules, trehalose and other substances known for protecting molecules from desiccating forces can be used. As shown herein, viral particles can be coated, thus it is possible to coat nanoparticles and microparticles since these might enhance the immune responses. Delivery efficiencies can be evaluated, and imaging can be used to characterize the coatings.

Develop a new paradigm for peanut allergen immunotherapy. The mouth is the first place where food makes contact with the body, and the chewed food particles have the potential to enter the gingival crevice and subsequently the tissues through the junctional epithelium. It is thus not surprising that the immune network in the gingiva may have a major role in maintaining tolerance. Indeed, proof-of-concept study using the coated floss for peanut allergen immunotherapy decreased sensitization. This approach provides for the rapid development of allergen immunotherapy for peanut and other food allergens. A floss can also be used for, e.g., peanut allergen immunotherapy by targeting junctional epithelium. The effect of dose of peanut allergen, frequency of flossing, use of adjuvants, use of particles to enhance phagocytosis and antigen processing, and delayed release coatings will be studied in the context of immunotherapy.

Administration into the gingival crevice can only be done after tooth eruption, which in humans occurs at 6-12 months. While the proposed paradigm may not become a mainstay in childhood vaccines until an infant is about 1 year old, the amplified immune responses resulting from the new paradigm will certainly impact and inform vaccine development, which could help cancer and HIV vaccines, and offer superior treatment for allergies, which are treated later in life for safety, and autoimmune diseases, which often appear late in life.

FIGS. 1A to 1F show the oral cavity route of immunization: (FIG. 1A) Human mouth. (FIG. 1B) Structure of gingival crevice and junctional epithelium (JE). (FIG. 1C) Delivery of active agent to junctional epithelium in gingival crevice and the diffusion of active agent in junctional epithelium and adjacent tissue over time, (FIG. 1D) delivery of antigen molecule coated on floss and effect of flossing on mouse gum tissue, and (FIG. 1E) diffusion of ovalbumin (Ova) conjugated to rhodamine in gum tissue. Flossing is performed, on each of the incisor tooth, by placing antigen deposited floss around the tooth and flossing for ten times so that the coated antigen gets deposited on the gum line. (FIG. 1F) Delivery efficiency of floss coated with fluorescein isothiocyanate (FITC) conjugated ovalbumin (Ova).

Targeting Junctional Epithelium in the Gingival Crevice for Vaccination Against Infectious A gents.

Example 1: Floss Mediated Delivery of Ovalbumin (Ova) to the Junctional Epithelium (JE) Induces Strong Systemic and Mucosal Antibody Response in Mice (Vaccine Angle)

Figure 2A:
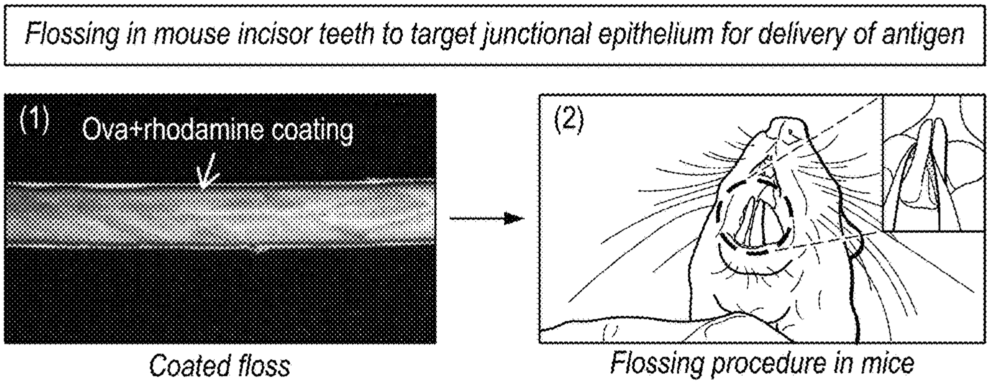
FIGS. 2A to 2G show floss-mediated vaccine delivery and characterization of immune response.
Figure 2B:
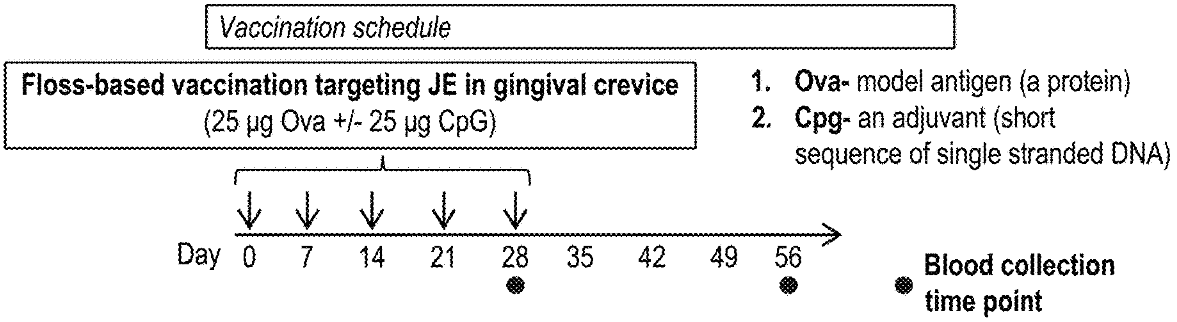
Figure 2C:
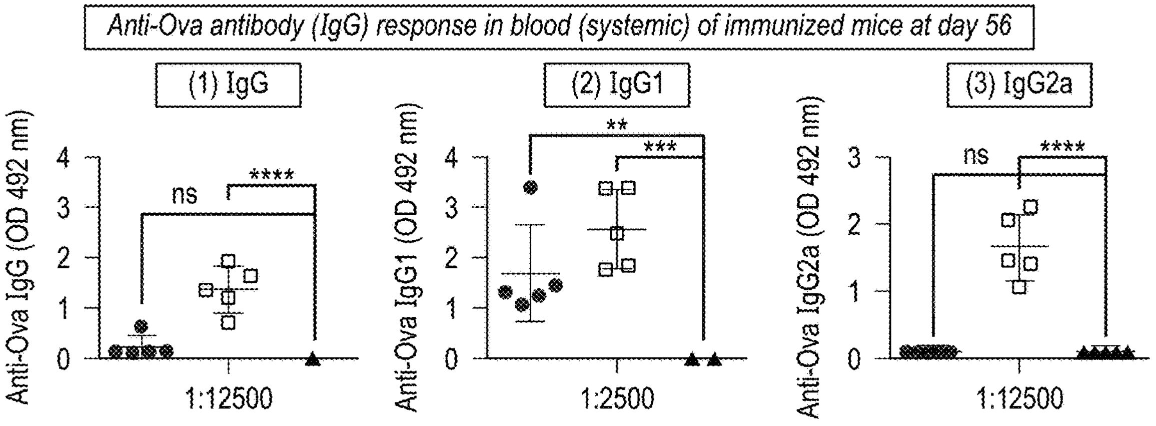
Figure 2D:
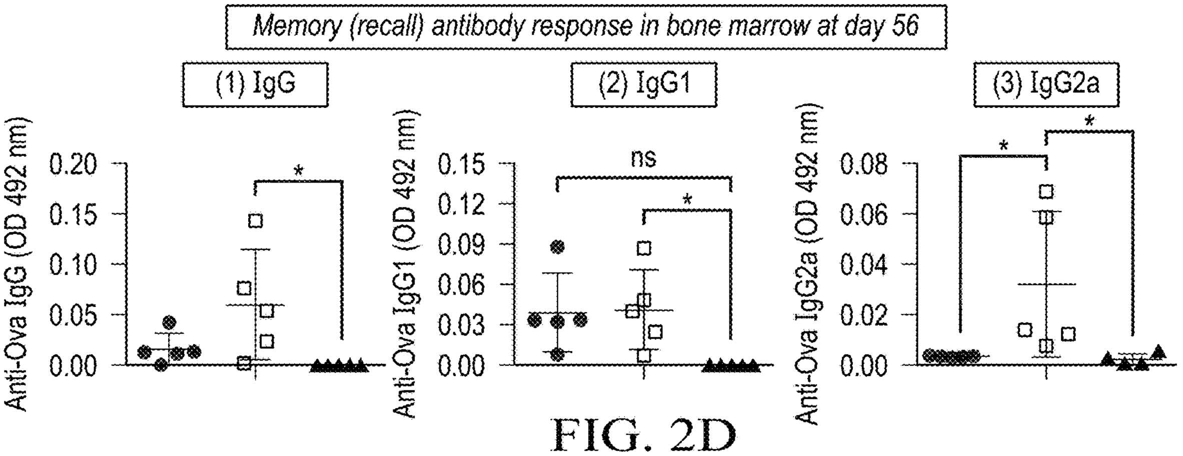
Figure 2E:
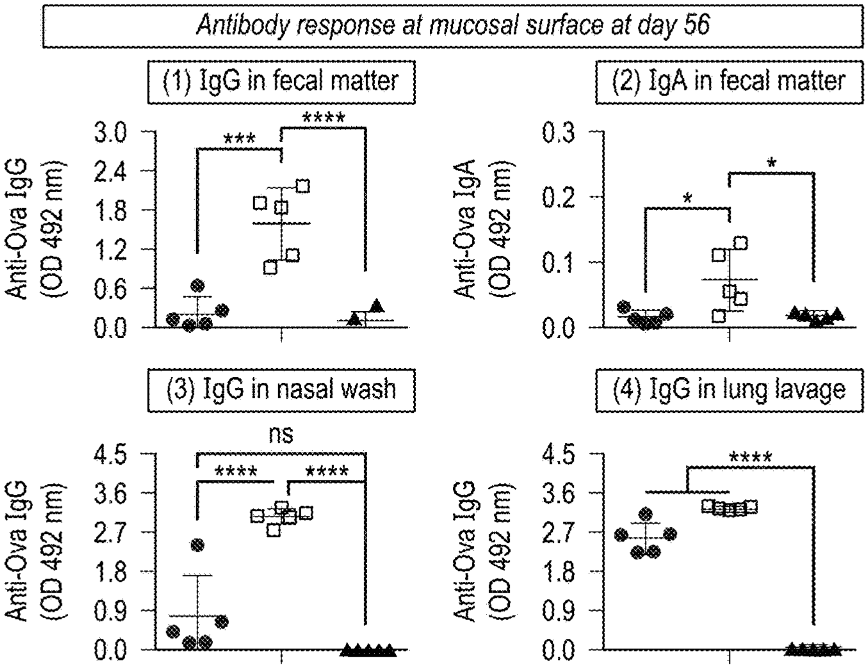
Figure 2F:
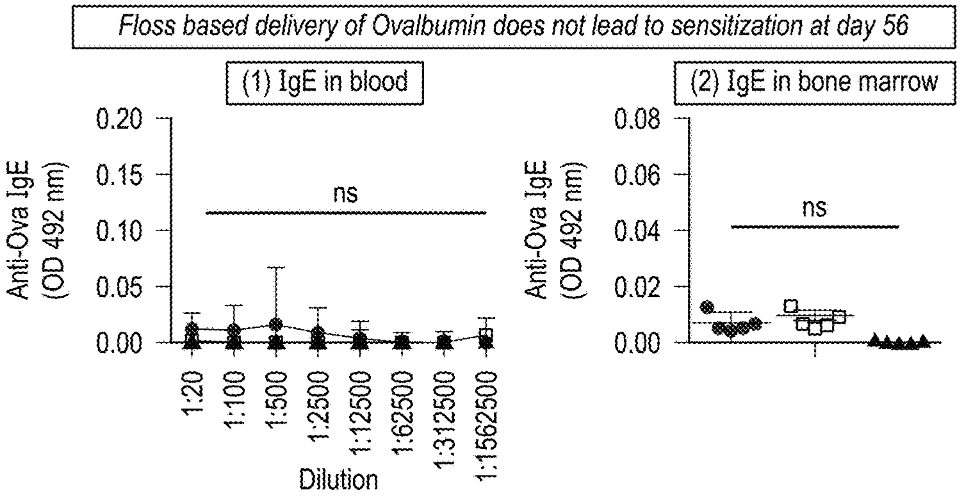
Figure 2G:
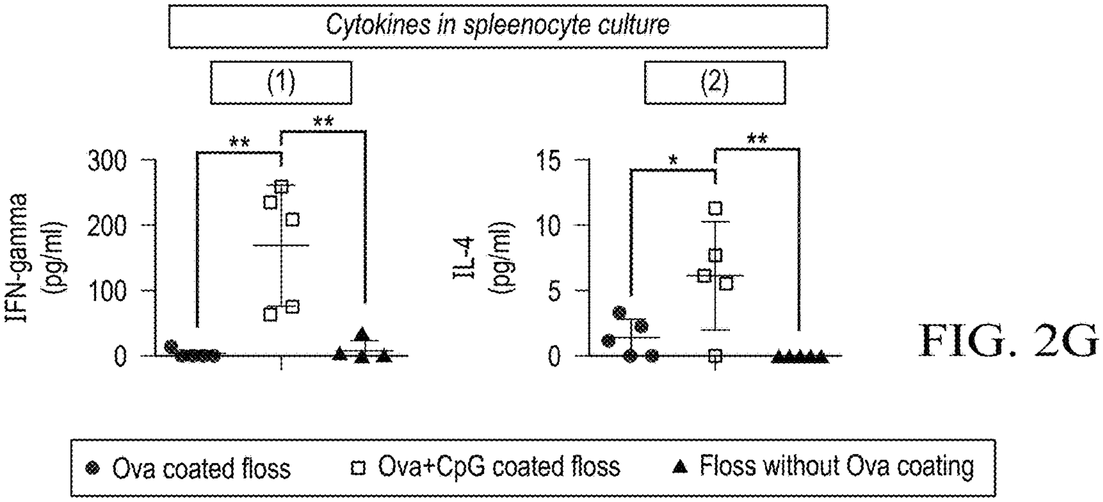

FIGS. 2A to 2G show floss-mediated vaccine delivery and characterization of immune response. (FIG. 2A)(1) Coated floss stereomicrograph and FIG. 2A(2) flossing procedure in mice. (FIG. 2B) Vaccination schedule: Balb/c mice (n=5) were vaccinated by flossing antigen (Ovalbumin (Ova), a model antigen) deposited floss on their gums. Floss included a deposit of 25 μg Ova+/−25 μg CpG (single-stranded oligodeoxynucleotide adjuvant) and mice were vaccinated weekly, up to 4 weeks total. Mice treated with floss without any coating were treated as control. Systemic immune response: Mice were bled at day 28 and 56, and anti-Ova antibody response (at either 1:12500 or 1:2500 dilution) in serum was analyzed through enzyme-linked immunosorbent assay (ELISA). FIG. 2(C)(1)-(3) Anti-Ova antibody response at day 56-FIG. 2(C)(1) IgG, FIG. 2(C)(2) IgG 1 and FIG. 2(C)(3) IgG2a. Individual mouse serum was used in analysis. FIG. 2(D)(1)-(3) shows the memory immune response: Vaccinated mice were euthanized, and bone marrow cells were collected. Cells were cultured in triplicates in a concentration of $1\times10^6$ cells per well with RPMI medium supplemented with 10% fetal bovine serum and penicillin-streptomycin antibiotics. Supernatant of cultured cells were collected post 96 h and anti-Ova responses were analyzed. FIG. 2(D)(1)-(3) Anti-Ova antibody response in bone marrow cells-FIG. 2(D)(1) IgG, FIG. 2(D)(2) IgG1, FIG. 2(D)(3) IgG2a. This result suggests that the response is not just local and systemic but was able to induce a memory response to better prepare individual for future exposure to same antigen (Ag). FIG. 2(E)(1)-(4) show the mucosal immune response. At day 56, fecal matter, nasal wash and lung lavage were collected from the vaccinated and mice that were treated with floss only. Anti-Ova FIG. 2(E)(1) IgG in fecal matter (1:5 dilution), FIG. 2(E)(2) IgA in fecal matter (1:5 dilution), FIG. 2(E)(3) IgG in nasal wash (undiluted), and FIG. 2(E)(4) IgG lung lavage (undiluted). FIG. 2(F)(1)-(2) No significant amount of IgE was detected either (1) in the serum or (2) in the bone marrow of the mice vaccinated through floss indicating that the target site of JE does not sensitize the individual against the delivered Ag. FIG. 2(G) Vaccinated mice were euthanized and splenocyte cells were collected. Cells were cultured, re-stimulated by Ova (200 μg/ml) in triplicates in a concentration of $1\times10^6$ cells per well with RPMI medium supplemented with 10% fetal bovine serum and penicillin-streptomycin antibiotics. Supernatant of cultured cells were collected post 96 h and cytokine levels were analysed. FIG. 2(G) shows cytokine levels in splenocyte culture, FIG. 2(G)(1) IFN-gamma, and FIG. 2(G)(2) IL-4. Data represented as mean±SD. One-way ANOVA test was used to compare between the groups at different serum dilutions. *p<0.05, p<0.01, *p<0.001, and **p<0.0001.

Figure 3A:
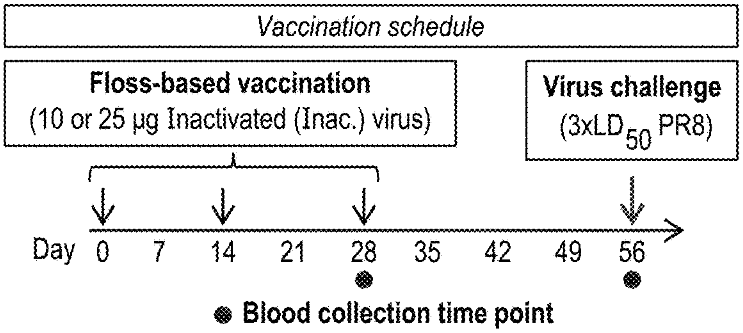
FIGS. 3A to 3C show a floss for influenza vaccination.
Figure 3B:
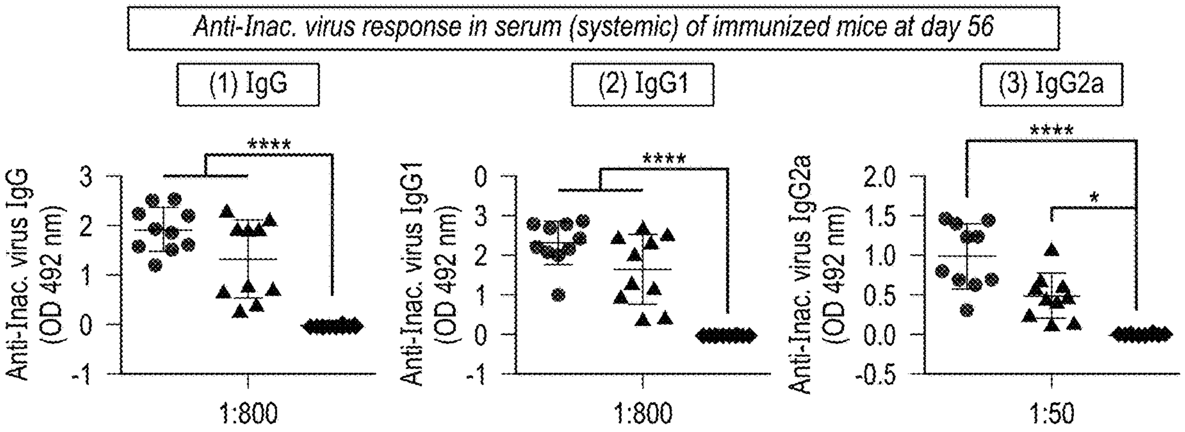
Figure 3C:
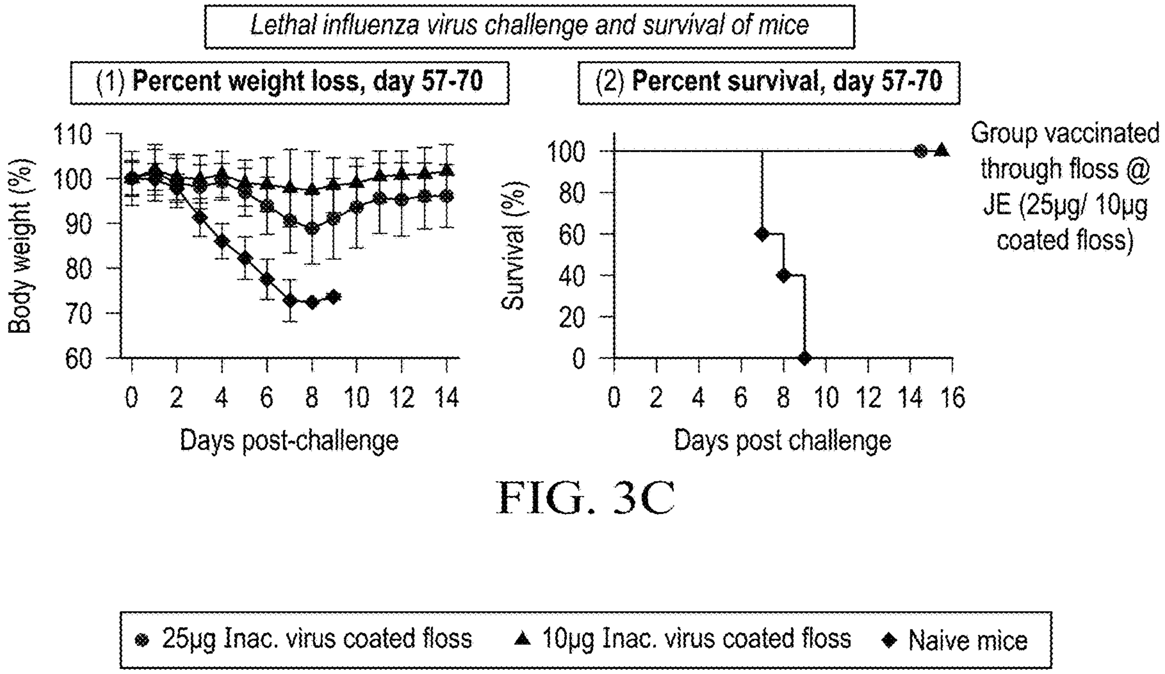

€Example 2: Floss Mediated Delivery of Inactivated (Inac.) Influenza Virus to the Junctional Epithelium (JE) Induces Strong Systemic Antibody Response and Protects Mice from a Lethal Challenge FIGS. 3A to 3C show a floss deposited for influenza vaccination. FIG. 3(A) Vaccination schedule: Balb/c mice (n=10) were vaccinated either with 10 μg or 25 μg of Inactivated (Inac.) virus coated on a floss for a total of three times-once on each of day 0, 14 and 28. At day 56, mice were bled and anti-Inac. virus immune response (at either 1:800 or 1:50 dilution) was analyzed through ELISA. FIG. 3(B)(1)-(3) Anti-Inac. virus FIG. 3(B)(1) IgG, FIG. 3(B)(2) IgG1, FIG. 3(B)(3) IgG2a antibody response in serum at day 56. Virus challenge: At d56, mice were challenged with $3\times LD_{50}$ (lethal dose 50%) of A/PR/8/34 (H1N1) influenza virus. Individual mice samples were used in analysis. Data represented as mean±SD. One-way ANOVA test was used to compare between the groups. *p<0.05, p<0.01, *p<0.001, and ****p<0.0001. FIG. 3(C)(1)-(2) Mice were observed every day for change in the body weight and severity of infection. FIG. 3(C)(1) Percent change in body weight, FIG. 3(C)(2) percent survival rate of vaccinated mice after infection. n=5 mice in each group.

Figure 4A:
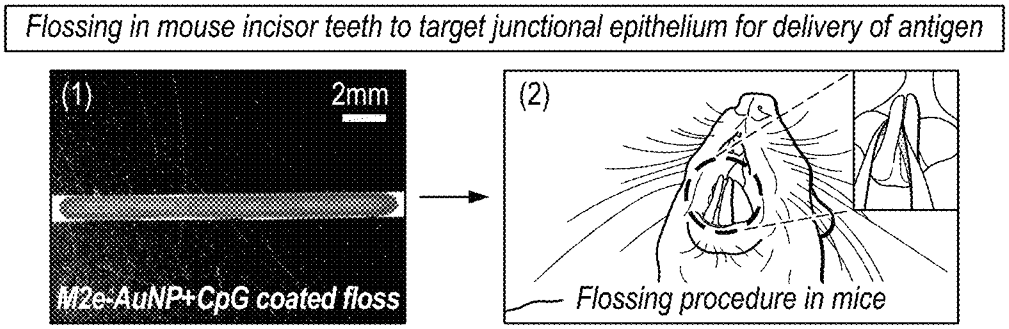
FIGS. 4A to 4D show floss-mediated delivery of M2e-AuNP+CpG (MAC), a vaccine formulation consisting of a peptide (M2e) conjugated to gold nanoparticles (AuNP's) further supplemented with an adjuvant (CpG), vaccine and characterization of immune response.
Figure 4B:
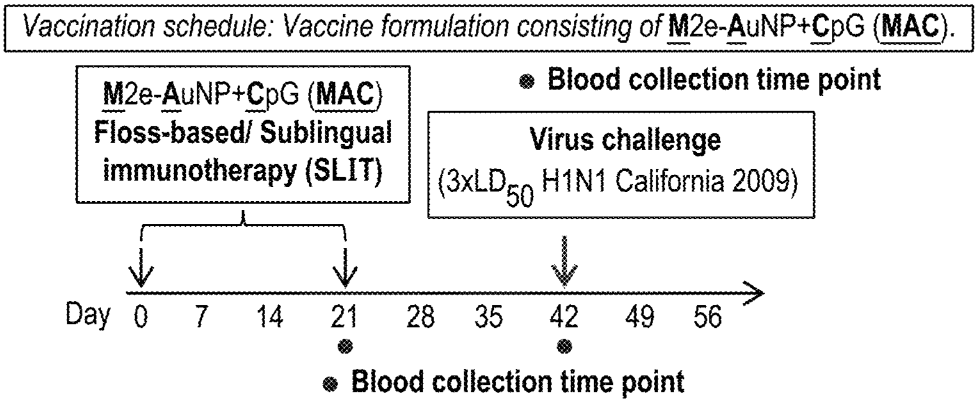
Figure 4C:
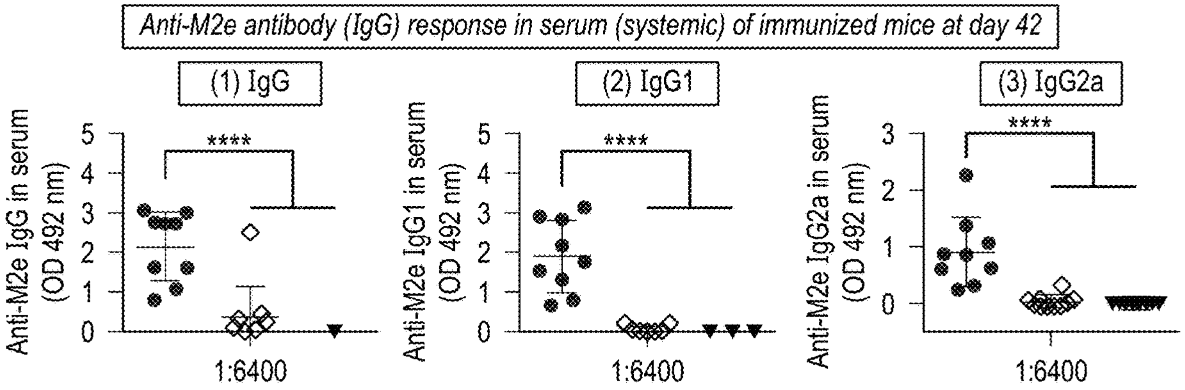
Figure 4D:
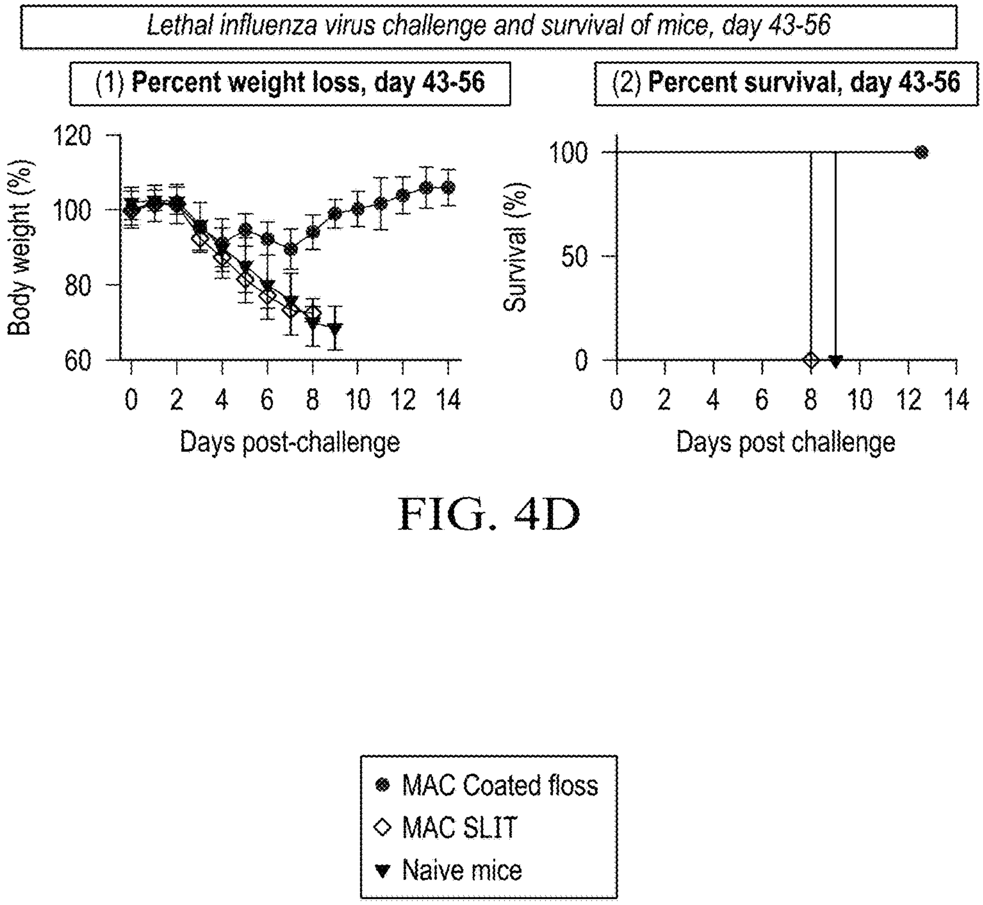

Example 3: Floss Mediated Delivery of M 2e Gold Nanoparticle (AuNP) Conjugate Based Universal Influenza Vaccine to the Junctional Epithelium (JE) Induces Strong Systemic Antibody Response and Protects Mice from a Lethal Challenge FIGS. 4A to 4D show floss-mediated delivery of M2e-AuNP+CpG (MAC), a vaccine formulation consisting of a peptide (M2e) conjugated to gold nanoparticles (AuNP's) further supplemented with an adjuvant (CpG), vaccine and characterization of immune response. FIG. 4(A)(1) Stereomicrograph of floss coated with M2e-AuNP+CpG containing 56 μg of AuNP's, 8.1 μg of M2e and 20 μg of CpG (1× dose) and FIG. 4(A)(2) flossing procedure in mice. FIG. 4(B) Vaccination schedule: Balb/c mice (n=10) were vaccinated by either flossing vaccine formulation [M2e-AuNP+CpG (MAC)] coated floss on their gums or by placing the vaccine formulation [M2e-AuNP+CpG (MAC)] under tongue [sublingual immunotherapy (SLIT)]. Vaccine formulation (MAC), either coated on floss or delivered through SLIT, consisted of 56 μg of AuNP's, 8.1 μg of M2e and 20 μg of CpG (single-stranded oligodeoxynucleotide adjuvant) and mice were vaccinated on day 0 and day 21. Naïve mice that received no treatment were treated as control. Systemic immune response: Mice were bled at day 21 and 42, and anti-M2e antibody response (at 1:6400 dilution) in serum was analyzed through enzyme-linked immunosorbent assay (ELISA). FIG. 4C(1)-(3) Anti-M2e antibody response in serum at day 42-FIG. 4C(1) IgG, FIG. 4C(2) IgG1 and FIG. 4C(3) IgG2a. Individual mouse serum was used in analysis. Data represented as mean±SD. One-way ANOVA test was used to compare between the groups. *p<0.05, p<0.01, *p<0.001, and ****p<0.0001. Virus challenge. (FIG. 4D(1)-(2)) At day 43, mice were challenged with $3\times LD_{50}$ (lethal dose 50%) of A/California/07/2009 H1N1 virus. Mice were observed every day for change in the body weight and severity of infection. FIG. 4D(1) Percent change in body weight, FIG. 4D(2) percent survival rate of vaccinated mice after infection. n=5 mice in each group.

Targeting Junctional Epithelium in the Gingival Crevice for Allergen-Specific Immunotherapy.

Example 4: Floss Mediated Delivery of Peanut Extract (PE) to the Junctional Epithelium (JE) Induces Strong Systemic and Mucosal Antibody Response in Mice (Vaccine Angle)

Figure 5A:
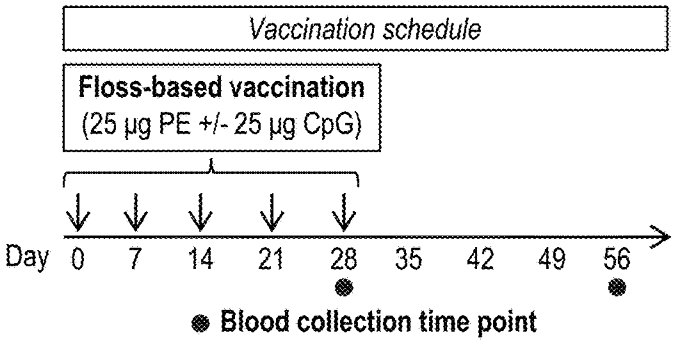
FIGS. 5A to 5E show floss-mediated vaccine delivery and characterization of immune response.
Figure 5B:
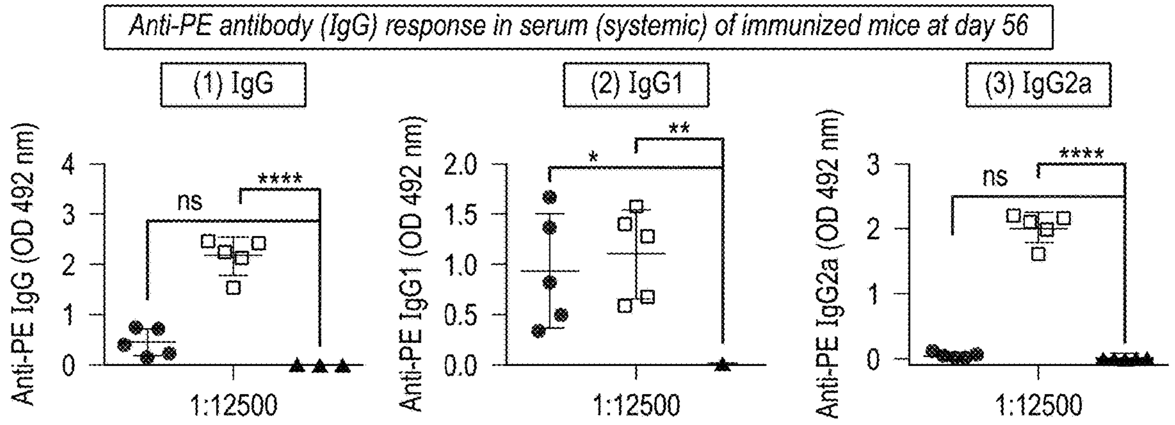
Figure 5C:
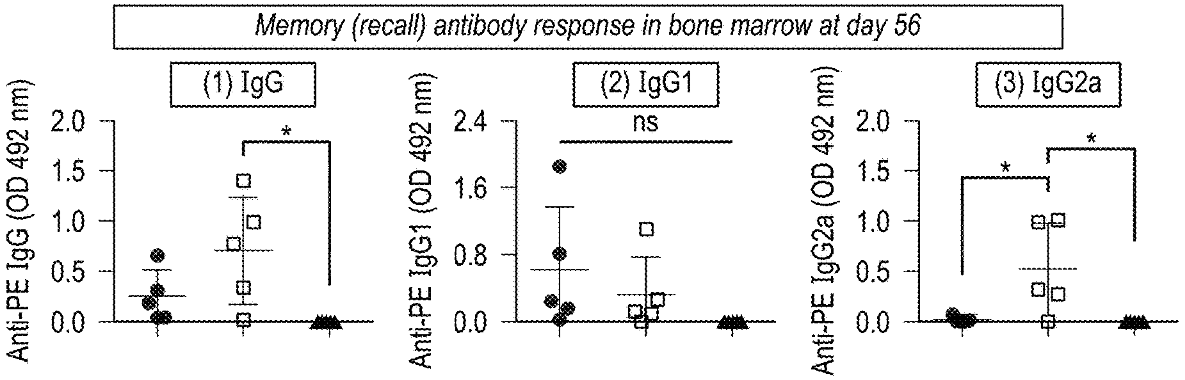
Figure 5D:
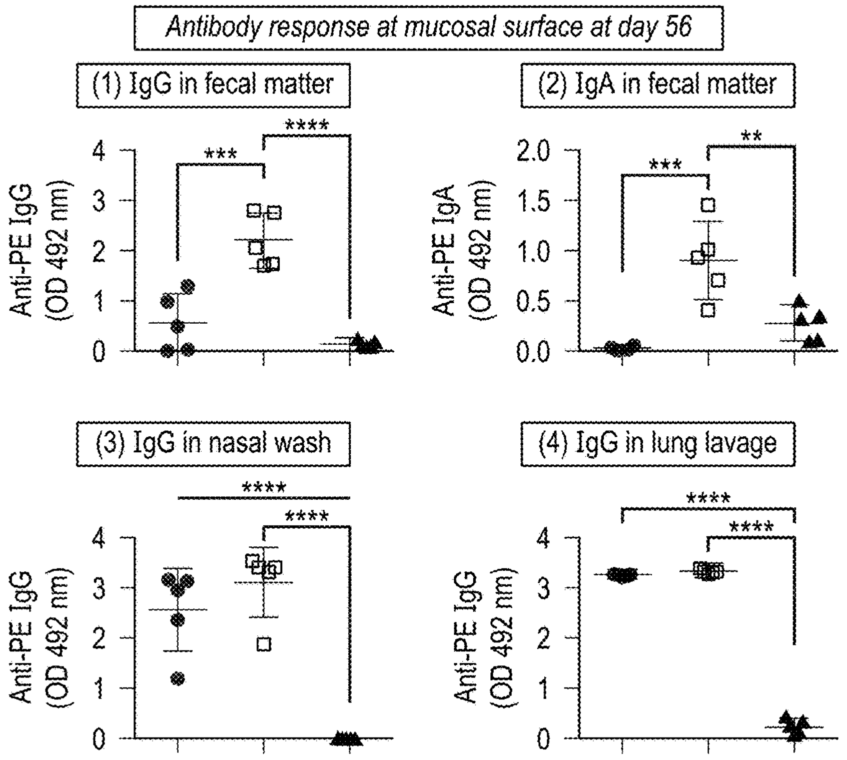
Figure 5E:
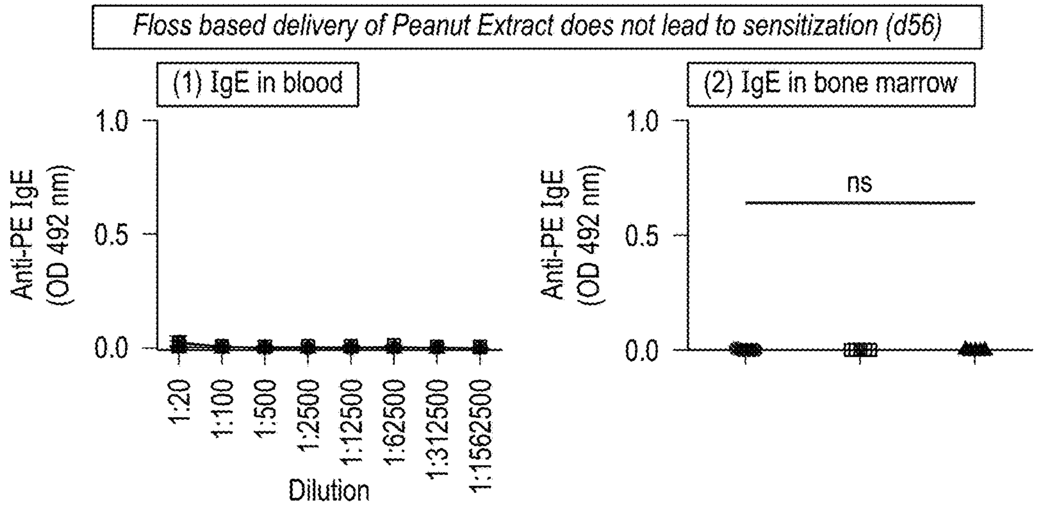

FIGS. 5A to 5E show floss-mediated vaccine delivery and characterization of immune response. (FIG. 5A) Vaccination schedule: Balb/c mice (n=5) were vaccinated by flossing antigen (Peanut extract (PE)) deposited floss on their gums. Floss was deposited with 25 μg PE+/−25 μg CpG (single-stranded oligodeoxynucleotide adjuvant) and mice were vaccinated weekly, up to 4 weeks total. Mice treated with floss without any coating or deposits were treated as control. Systemic immune response: Mice were bled at day 28 and 56, and anti-PE antibody response (at 1:12500 dilution) in serum was analyzed through enzyme-linked immunosorbent assay (ELISA). FIG. 5B(1)-(3) Anti-PE antibody response in serum at day 56-FIG. 5B(1) IgG, FIG. 5B(2) IgG1 and FIG. 5B(3) IgG2a. Individual mouse serum was used in analysis. (FIG. 5C(1)-(3)) Memory Immune response: Vaccinated mice were euthanized, and bone marrow cells were collected. Cells were cultured in triplicates in a concentration of $1\times10^6$ cells per well with RPMI medium supplemented with 10% fetal bovine serum and penicillin-streptomycin antibiotics. Supernatant of cultured cells were collected post 96 h and anti-PE responses were analyzed. Anti-PE FIG. 5C(1) IgG, FIG. 5C(2) IgG1, FIG. 5C(3) IgG2a. This result suggests that the response is not just local and systemic but was able to induce a memory response to better prepare individual for future exposure to same antigen (Ag). (FIG. 5D) Mucosal immune response. At day 56, fecal matter, nasal wash and lung lavage were collected from the vaccinated and naïve mice. Anti-PE FIG. 5D(1) IgG in fecal matter (1:5 dilution), FIG. 5D(2) IgA in fecal matter (1:5 dilution), FIG. 5D(3) IgG in nasal wash (undiluted), and FIG. 5D(4) IgG lung lavage (undiluted). (FIG. 5E(1)-(2)) No significant amount of IgE was detected either FIG. 5E(1) in the serum or FIG. 5E(2) in the bone marrow of the mice vaccinated through floss indicating that the target site, junctional epithelium, does not sensitize the individual against the delivered Ag. Data represented as mean±SD. One-way ANOVA test was used to compare between the groups at different serum dilutions. *p<0.05, p<0.01, *p<0.001, and ****p<0.0001.

Example 5: Floss Mediated Delivery of Peanut Extract (PE) to the Junctional Epithelium (JE) Induces Strong Systemic Antibody Response in Mice (Therapeutic Regime). Targeting JE for Immunotherapy of 'Food Allergies'

Figure 6A:
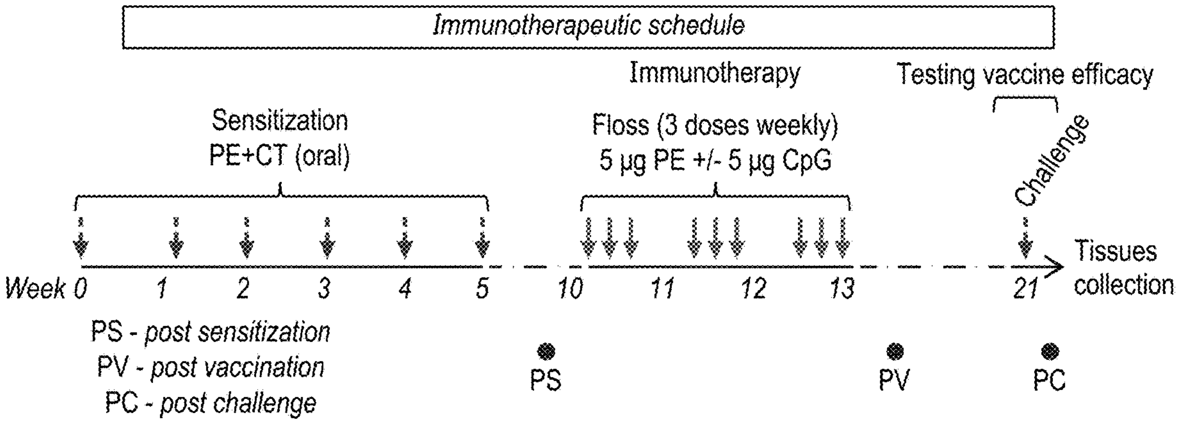
FIGS. 6A to 6D show a peanut allergen immunotherapy schedule.
Figure 6B:
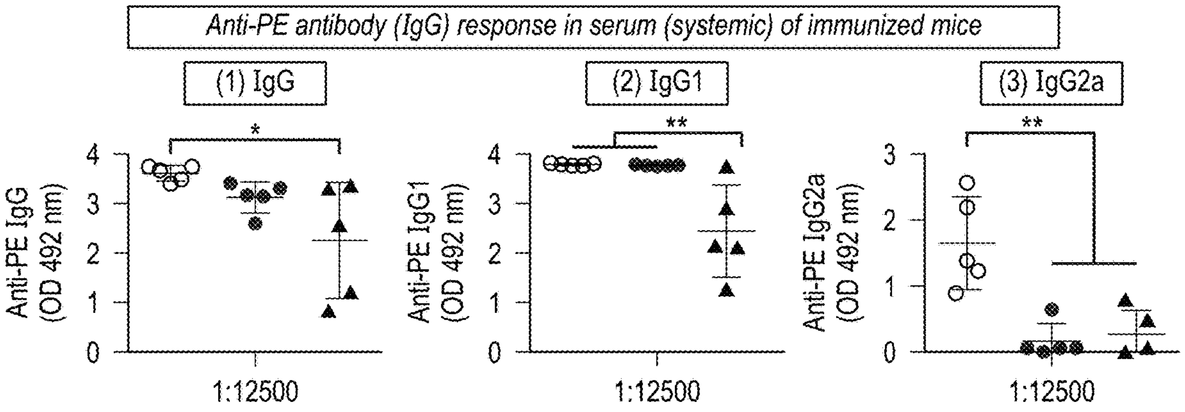
Figure 6C:
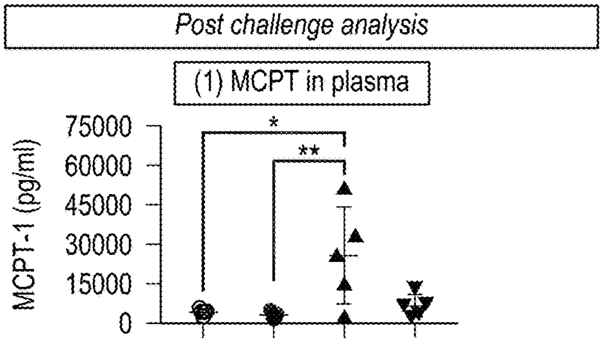
Figure 6D:
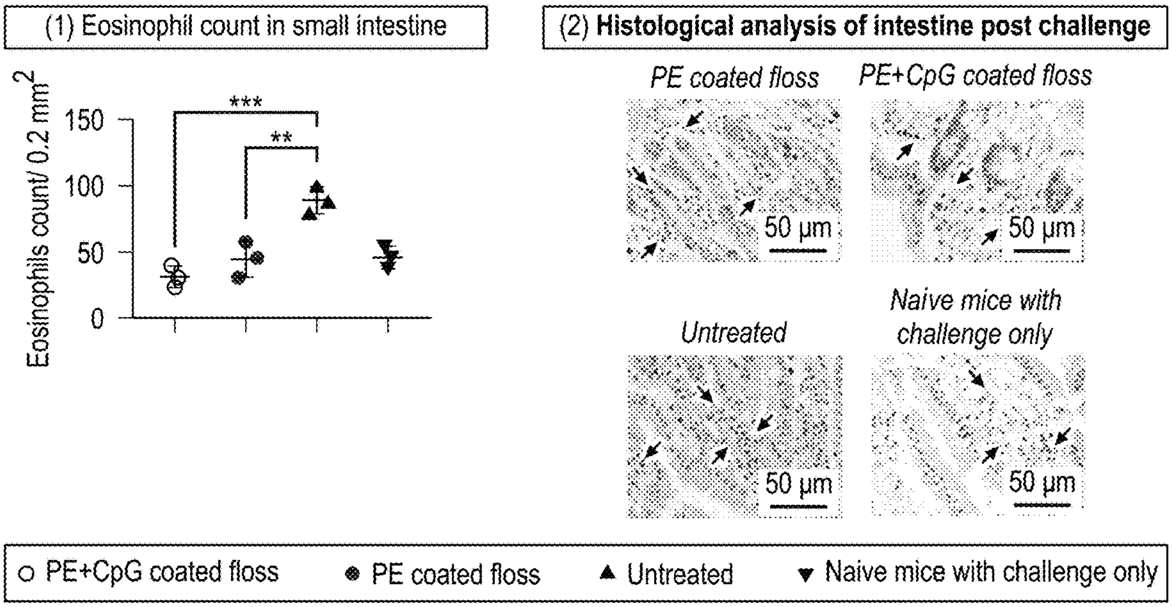
Figure 7A:
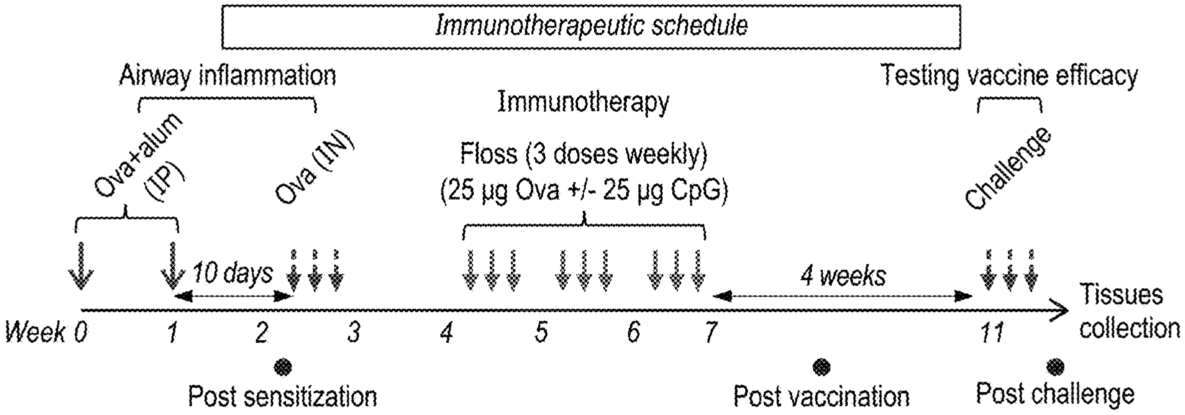

FIGS. 6A to 6D show a peanut allergen immunotherapy schedule. (FIG. 6A) Immunotherapeutic schedule: Balb/c mice (n=5) were sensitized through oral route [1 mg peanut extract (PE)+15 μg cholera toxin (CT)], given at intervals of a week for five consecutive weeks. Mice were then vaccinated by flossing antigen-coated floss. Floss was coated with 5 μg PE+/−5 μg CpG (single-stranded oligodeoxynucleotide adjuvant) and mice were vaccinated three times per week, up to 3 weeks total. Sensitized mice that did not receive any treatment were kept as control (untreated). Mice were bled at day 10 post-vaccination (PV). Mice were challenged eight weeks post-vaccination with PE allergen (500 μg) through intraperitoneal route (IP), were then euthanized and different tissues were collected. (FIG. 6B(1)-(3)) Anti-PE antibodies in serum (at 1:12500 dilution) were confirmed through enzyme-linked immunosorbent assay (ELISA). Anti-PE FIG. 6B(1) IgG, FIG. 6B(2) IgG1 and FIG. 6B(3) IgG2a antibody response at day 10 post-vaccination. Individual mouse serum was used in analysis. Data represented as mean±SD. One-way ANOVA test was used to compare between the groups at different serum dilutions. *p<0.05, p<0.01, *p<0.001, **p<0.0001. and ns: not significant. PE induced anaphylaxis. (FIG. 6C) (1) Plasma MCPT-1 levels post IP challenge with PE. Histological analysis of intestinal tissue. (FIG. 6D) Eight weeks post-vaccination, mice were challenged with PE allergen (500 μg) through intraperitoneal route. Mice were then euthanized, and small intestine was collected from proximal, middle and distal ends, fixed, dehydrated and embedded in paraffin wax for cutting. Tissue sections were stained with hematoxylin and eosin (H & E) stain and sectioned for histology. FIG. 6D(1) Number of eosinophils counted in respective sections from mice of different treatment groups. FIG. 6D(2**) Brightfield image of H & E stained intestine with arrows pointing to eosinophil infiltration. Individual mouse sample was used in analysis. Data represented as mean±SD. One-way ANOVA was used to compare between the groups. *$p<0.05$, $p<0.01$, *$p<0.001$ and ns: not significant.

Example 6: Floss Mediated Delivery of Ovalbumin (Ova) to the Junctional Epithelium (JE) Induces Strong Systemic Antibody Response in Mice (Therapeutic Regime). Targeting JE for Immunotherapy of 'Airway Allergies'

FIGS. 7A to 7D show airway allergen immunotherapy. (FIG. 7A) Immunotherapeutic schedule: Balb/c mice (n=5) were sensitized through two intraperitoneal (IP) injection (25 μg Ova+2 mg of alum (an adjuvant)), given at interval of a week. Ten days post sensitization (PS), mice were challenged with Ova (50 μg) through intranasal route (IN) for three consecutive days to develop airway inflammation. Mice were then vaccinated by flossing antigen-deposited floss. Floss was coated with 25 μg Ova+/−25 μg CpG (single-stranded oligodeoxynucleotide adjuvant) and mice were vaccinated three times per week, up to 3 weeks total. Sensitized mice that did not receive any treatment were kept as control (untreated). Mice were bled at day 10 post-vaccination. Mice were challenged on day 28 post-vaccination with Ova allergen (50 μg) through intranasal route (IN) for three consecutive days, were then euthanized and different tissues were collected Systemic immune response: (FIG. 7B(1)-(4)) Anti-Ova FIG. 7B(1) IgG, FIG. 7B(2) IgG1, FIG. 7B(3) IgG2a and FIG. 7B(4) IgE antibody response in serum (at either 1:12500 or 1:500 or 1:20 dilution) at day 10 post-vaccination analyzed through enzyme-linked immunosorbent assay (ELISA). (FIG. 7C) Lung lavage analysis post-challenge. Mice were then euthanized, and mucosal secretion of lung lavage was collected. Cell count of FIG. 7C(1) eosinophils and FIG. 7C(2) neutrophils in lung lavage-cells were stained with diff-stain kit and counted by observing cells under confocal microscope. Histological analysis of lungs: (FIG. 7D) Mice were then euthanized, and lungs were harvested, fixed, cleaned and sectioned for histology. Tissue sections were stained with either periodic acid-Schiff (PAS) to stain for mucus deposition or trichrome blue (TCB) to stain for collagen deposition. Representative brightfield image of PAS stained lung (top panel) and TCB stained lung (bottom panel). Arrows in the top panel point to mucus deposition, and to collagen deposition in the bottom panel.

Example 7. Method/s for Deposits on Dental Floss

The majority of the floss available in the market are coated with a continuous coating of materials (such as wax, flavoring, etc.). Currently, the entire floss length (hundreds of feet in a floss cartridge) is coated. These coatings are not properly characterized and cannot be used for medical applications, because it is important to deliver a known quantity of the medication such as in the case of delivering a vaccine or delivering a drug/therapeutic molecule where deviations from recommended dose can be detrimental or may cause side effects.

The compositions and methods of the present invention address coating of any molecule in a simple manner through fluid dispensing. The method can be used to coat one or more active agents/molecules on the specific length of the floss, specific surfaces of the floss and even at a discrete location. Also, the method can be used to coat both sides if needed.

The present invention provides a novel way to coat a dental floss. A substance (for example a synthetic molecule or polymer, amino acid or its polymer, nucleotide or its polymer, lipids, carbohydrates, natural material, antigen/allergen/adjuvant/drug/combinations thereof) can be coated on surface of the floss for its delivery into the gum tissue. The delivery may have any intended use for example to modulate immune response, systemic effect, or local effect. Surface of the floss can be coated by depositing the biologics (the deposition process deposits on a single contiguous portion of the floss, or on two or more discrete portions of the floss with same or different spacing between the each said deposited region) over a shorter or a longer distance/length of floss (the deposition process comprises placing liquid drops on the floss, or dragging the liquid drop(s) on the floss to spread it over a certain distance/length on the floss using a pipette, or spray coating, or ink jet printing, or pipette based coating, or cartridge printing or a combination thereof), and letting the coating to dry. To substantiate the current invention, we have shown effectiveness and proof-of-concept using antigens/allergens/peptides/micro-particles/nano-particles/single stranded deoxyribonucleic acid (DNA). Varying amounts of the biologics can be coated on the surface of the floss. The coated material can be easily delivered into the gum tissue by a simple action of flossing.

For the purpose of medical application using a coated floss, it is important to have the following properties: (a) the coating should be consistent over the short length of the coated floss to enable consistent delivery into the gum pocket by the user; (b) known amounts of formulations should be coated on the floss; and/or (c) The coating should stay adhered to the surface until intended use.

Floss is often made of material that is hydrophobic (such as TEFLON® or NYLON®) and it is difficult to wet these surfaces using a coating solution. Because of poor wetting, continuous and uniform coatings are difficult to achieve on the floss. While many different solvents can be used to make the coating solution, water is preferred for biological material that must be coated on the floss, and water-based coating solutions are even harder to coat on the floss. However, non-aqueous solutions can also be used with the present invention in which the active agent is in a solvent that is not soluble in water (or partially soluble) and the active agent is deposited onto the floss, and the solvent is evaporated leaving the active agent.

Instead of making a continuous coating, discrete drops of liquid can be deposited on the floss surface. By doing so, there is less need to uniformly spread the coating across a length, and reproducible coatings and patterns can be achieved. (1) Drops can be placed on the floss using fluid dispensing systems (manual or automated or their combinations). For proof of concept, manual dispensing was done. (2) The surface of the floss maybe made hydrophilic (for example by coating with a hydrophilic polymer, or for example by oxygen plasma treatment, or other conventional surface treatment approaches that can change the surface energy of the floss surface to better allow for the spreading of the coating liquid. (3) Place the coating liquid on the floss surface. After a certain period and after sufficient solvent has evaporated, the liquid on the floss can be mechanically spread. After some solvent has evaporated, the viscosity of the coating liquid increases, and the ability to spread it over the floss improves.

Advantages of using dispensing system (manual, automated, or a combination thereof) for depositing floss: (1) lesser loss of depositing formulation as compared to spray/dip coating; (2) depositing of a precise amount; (3) depositing of multiple deposited formulations; and/or (4) surface modification of the floss can be avoided since even water-based solutions can be deposited as drops to create uniform patterns.

Spray or dip coating can lead to wastage of material. In contrast use of depositing into discrete deposits on the surface of the floss leads to almost none to minimal loss of material. With depositing on the floss, precise control (for example if the goal is to deposit a small spot say less than 1 mm in length/diameter of the floss) is difficult to achieve. However, with fluid dispensing, even nanoliter to picoliter amounts can be simply deposited on the floss at known and precise locations. With fluid dispensing, it is straightforward to also deposit different material(s) with a small gap between the different deposited spots. This level of accuracy and precision is difficult with spray/dip coating. The approach could be used to develop and build depositing devices, which may be placed in pharmacies, homes, or clinician offices. Furthermore, using the proposed invention, active agent with a different solvent requirement for solubility (for example, one active agent, an antigen, with water as a solvent whereas the other active agent, an adjuvant, with organic solvent requirement) can be deposited on floss.

Figure 8:
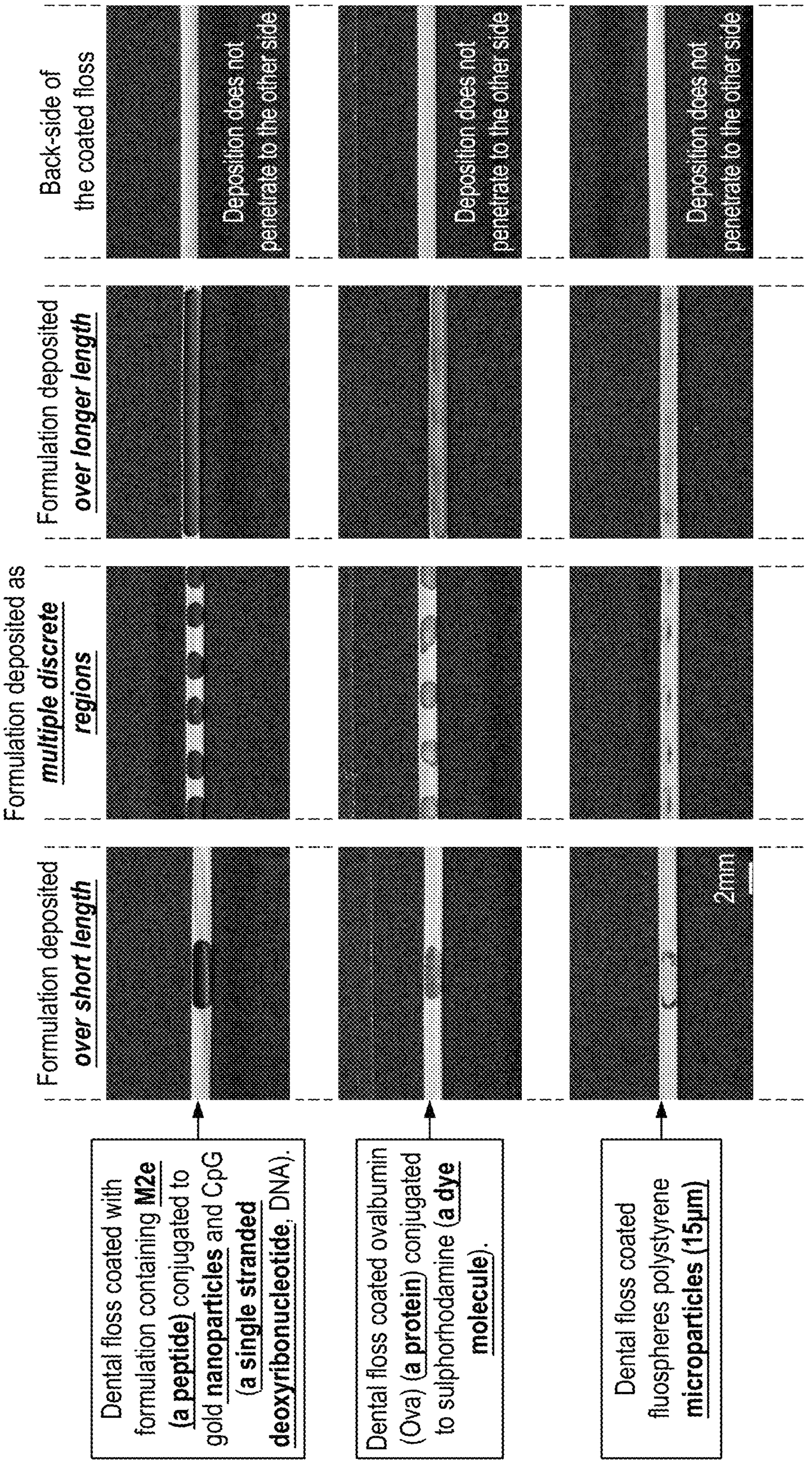
FIG. 8 shows the deposition capabilities, deposition of floss with peptide, nanoparticles, protein, oligonucleotide, microparticles, in different patterns of deposition either as a single region of deposition with a short length or a longer length, or multiple discrete regions of deposition, and only on one side of the floss.

FIG. 8 shows the deposition capabilities, deposition of floss with peptide, nanoparticles, protein, oligonucleotide, microparticles, in different patterns of deposition either as a single region of deposition with a short length or a longer length, or multiple discrete regions of deposition, and only on one side of the floss.

Figure 9:
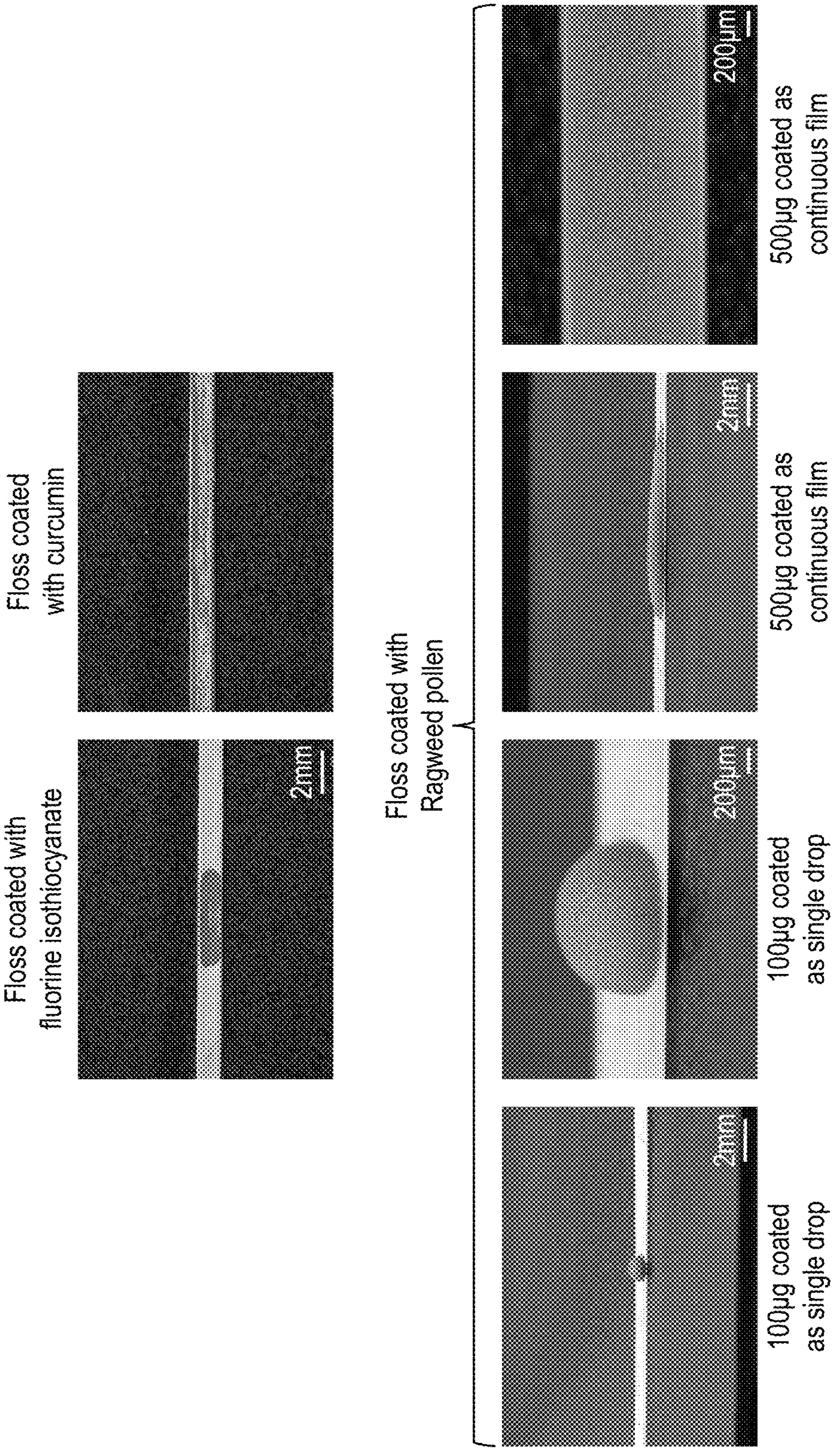
FIG. 9 shows the deposition capabilities, of depositing water soluble and water insoluble materials including pollen grain microparticles

FIG. 9 shows the deposition capabilities, of depositing water soluble and water insoluble materials including pollen grain microparticles.

Figure 10:
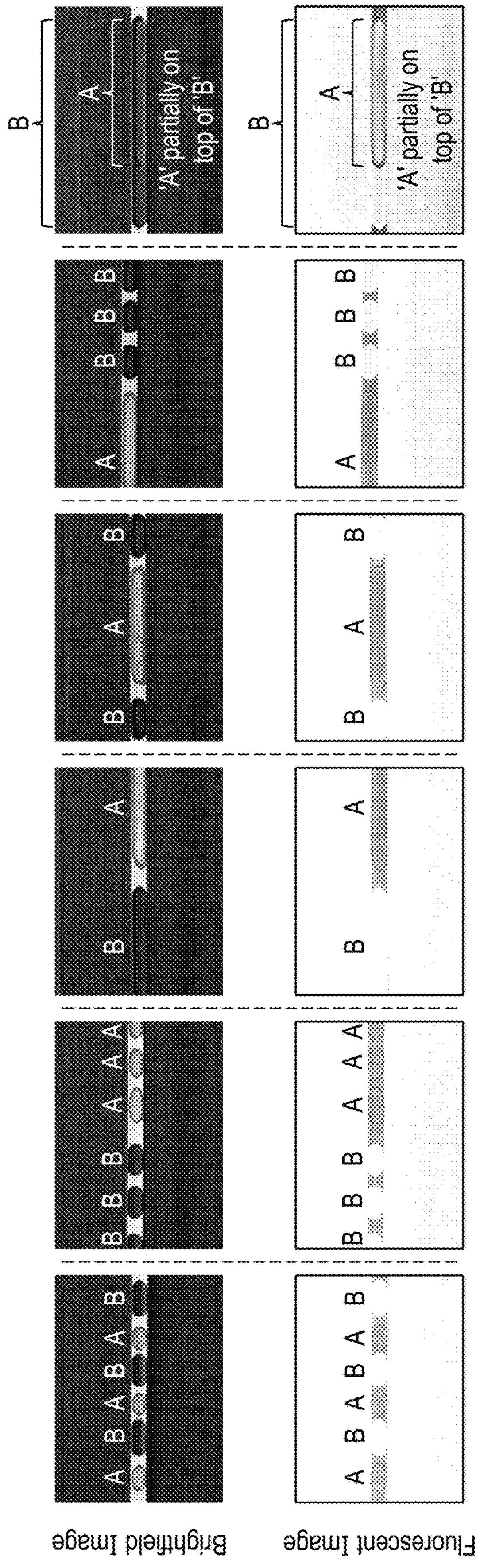
FIG. 10 shows the deposition capabilities, and different deposition patterns with two different compounds as example. One formulation was ovalbumin (protein) conjugated to NHS-Rhodamine (fluorescent reagent) in water—called as ‘A’, and second was M2e peptide conjugated to gold nanoparticles and CpG (single stranded DNA) in water—called as ‘B’.

FIG. 10 shows the deposition capabilities, and different deposition patterns with two different compounds as example. One formulation was ovalbumin (protein) conjugated to NHS-Rhodamine (fluorescent reagent) in water—called as 'A', and second was M2e peptide conjugated to gold nanoparticles and CpG (single stranded DNA) in water—called as 'B'.

Figure 11:
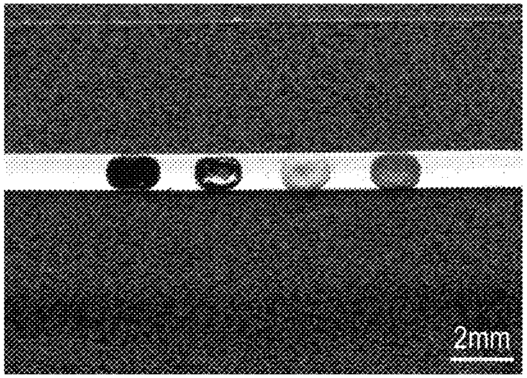
FIG. 11 shows the deposition capabilities of multiple materials, shown here are four different food colors (blue, green, yellow, red) deposited as four distinct portions.

FIG. 11 shows the deposition capabilities of multiple materials, shown here are four different food colors (blue, green, yellow, red) deposited as four distinct portions.

Figure 12:
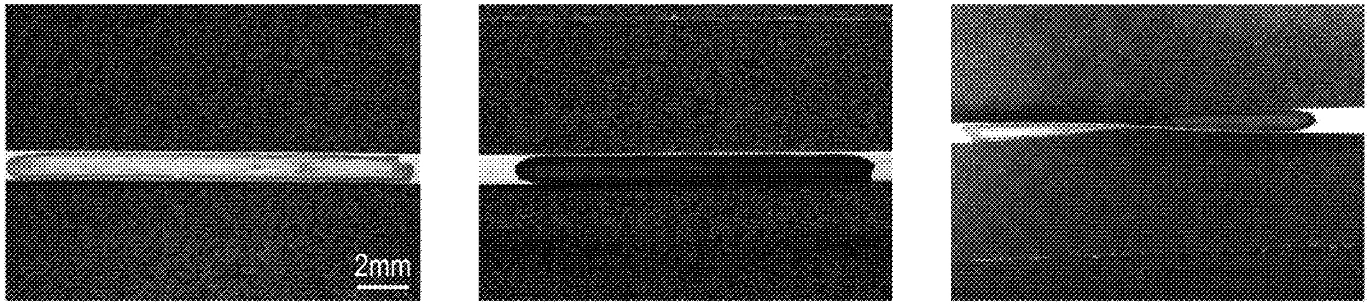
FIG. 12 shows the coating capabilities for coating two sides of floss with different formulations.

FIG. 12 shows the coating capabilities for coating two sides of floss with different formulations.

Figure 13:
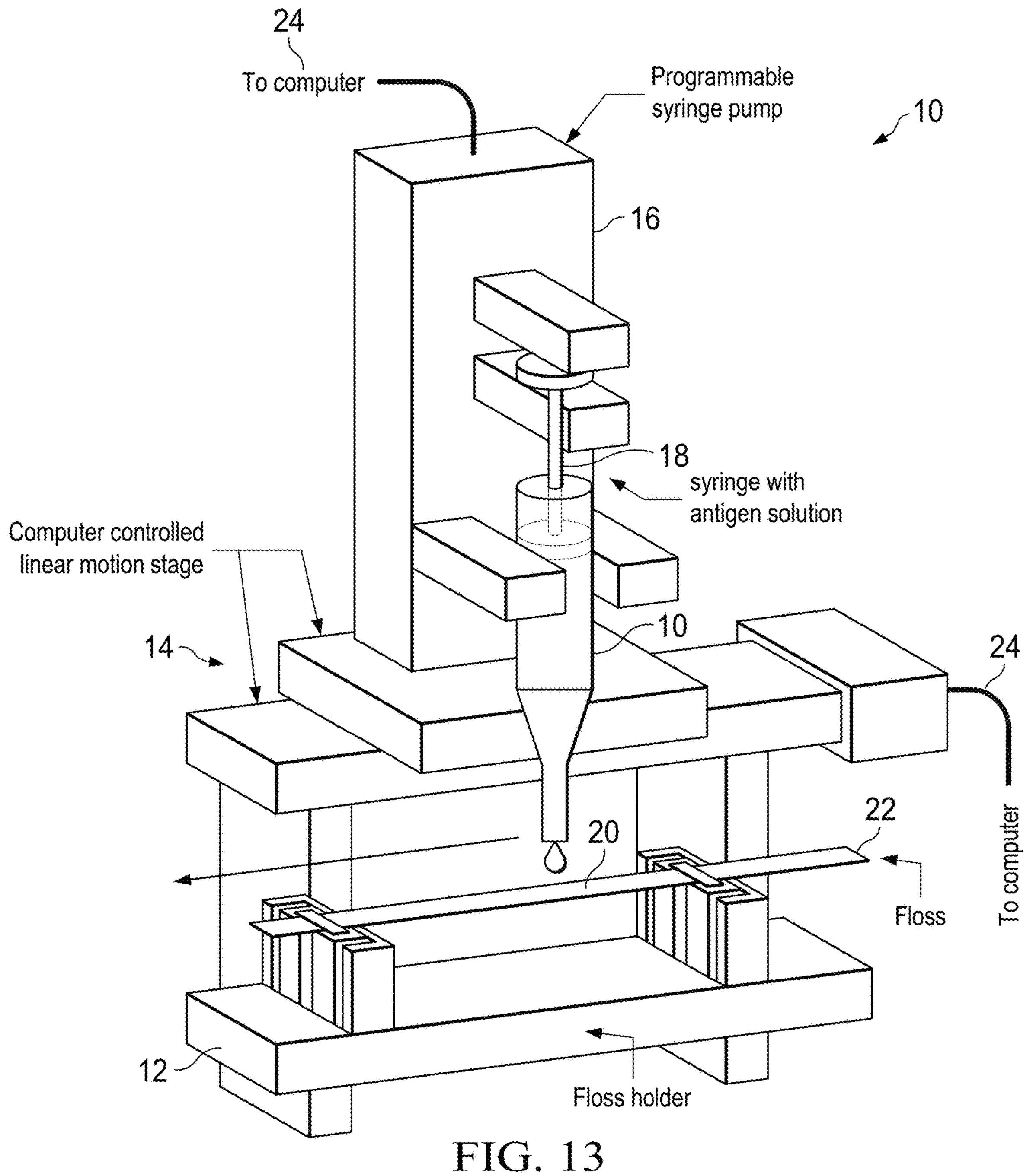
FIG. 13 shows an example of an automated coating station to coat floss.

FIG. 13 shows an example of an automated coating station 10 to coat floss. The automated coating station 10 includes a stand 12 that includes a controlled linear motion stage 14 that permits movement in one or two dimensions, shown in this embodiment with a two-dimensional stage, with a back 16 onto which a syringe assembly 18 is attached that controls the delivery of drop(s) 20 onto a floss 22. The stage is controlled by a computer 24, which can be connected to the controlled linear motion stage 14 and/or the syringe assembly 18.

Figure 14:
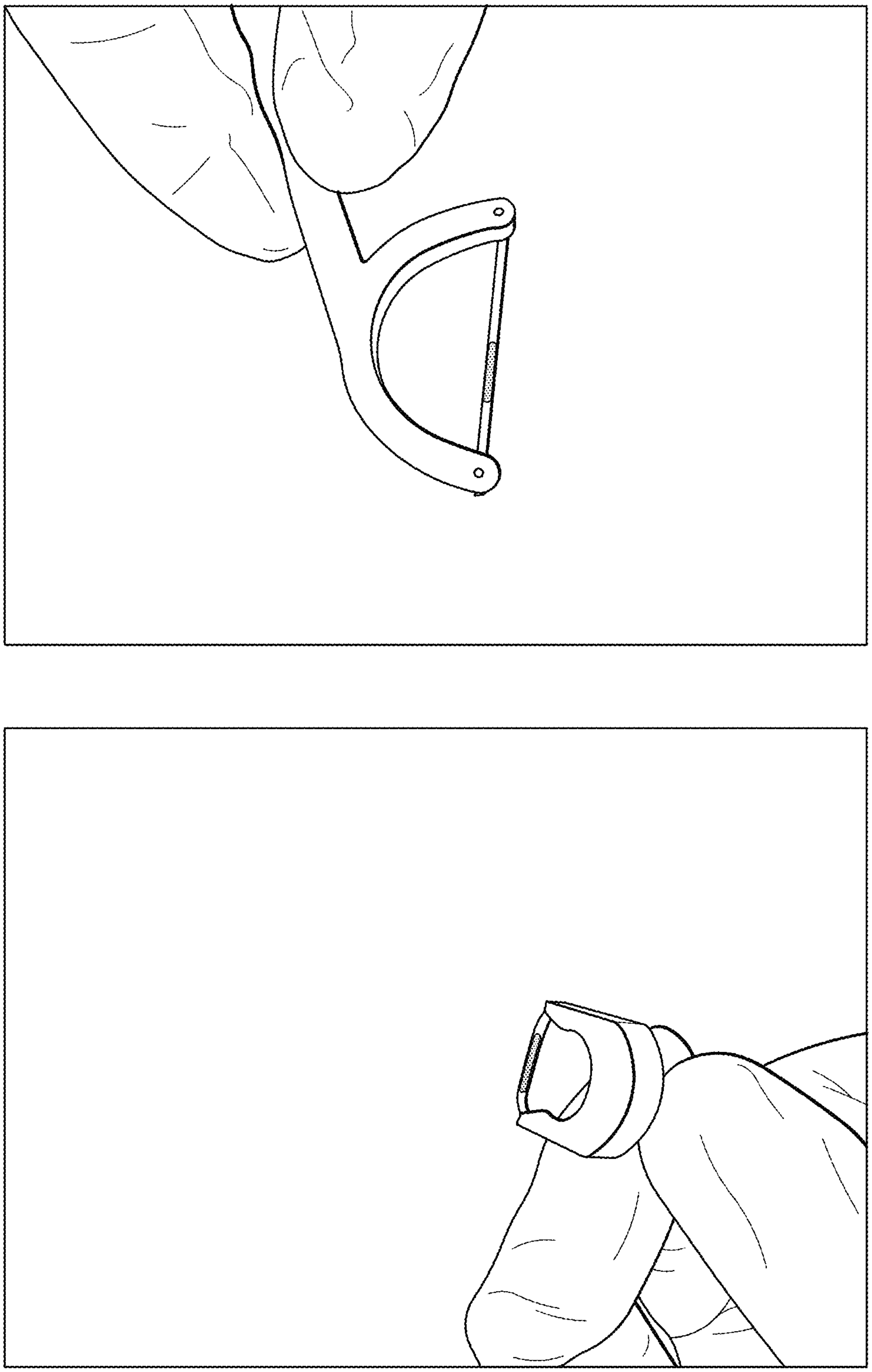
FIG. 14 shows two examples of the design of the flosser system.

FIG. 14 shows two examples of the design of the flosser system.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A device for triggering an immune response in a subject, comprising:

a floss configured to target delivery to a junctional epithelium of a gingival crevice, wherein the floss includes:

an effective amount of one or more antigens, immunogens, allergens, or combinations thereof, wherein the amount is sufficient to trigger an immune response in a subject;

a surface that is treated by changing the surface energy of the surface of the floss to promote adhesion of the one or more antigens, immunogens, allergens, or combinations thereof to the surface, wherein changing the surface energy of the surface of the floss includes exposing the surface to oxygen treatment, plasma treatment, or any combination thereof; and one or more excipients added to the one or more antigens, immunogens, allergens, or combinations thereof to enable controlled release of the one or more antigens, immunogens, allergens, or combinations thereof onto an apical aspect of the gingival crevice for absorption through the junctional epithelium;

a combination of a thickness of the floss and a thickness of the effective amount of the one or more antigens, immunogens, allergens, or combinations thereof is 500 microns or less, such that when the floss is inserted into the gingival crevice of the subject, the floss reaches the junctional epithelium at the apical aspect of the gingival crevice; and wherein the floss deposits, in response to reaching the junctional epithelium at the apical aspect of the gingival crevice, the effective amount of the one or more antigens, immunogens, allergens, or combinations thereof for absorption through the junctional epithelium of the gingival crevice of the subject, while excluding absorption through the vestibular mucosa, to obtain one or more of a mucosal and systemic immune response in the subject.

2. The device of claim 1, wherein at least one of:

the one or more antigens, immunogens, allergens, or combinations thereof are provided to maximize delivery of the one or more antigens, immunogens, allergens, or combinations thereof into the gingival crevice;

the one or more antigens, immunogens, allergens, or combinations thereof are provided repeatedly to a junctional epithelium of the gingival crevice;

the one or more antigens, immunogens, allergens, or combinations thereof is applied once or more than once with a frequency on a daily or weekly or monthly basis, such as 1, 2, 3, 4, 5, or 6 times daily or 1, 2, 3, 4, 5, 6, or 7 times weekly or 1, 2, 3, or 4 times monthly;

the one or more antigens, immunogens, allergens, or combinations thereof desensitize an individual to the antigens, immunogens, allergens, or combinations thereof by 10%, 20%, 30%, 40%, 50%, 60%, 70%, 80%, 90% or 100%;

the one or more antigens, immunogens, allergens, or combinations thereof trigger the immune response in the subject to the antigens, immunogens, allergens, or combinations thereof by between 0.1-100% to protect the subject to the one or more antigens, immunogens, or combinations thereof; or wherein between 0.001%-100% of the one or more antigens, immunogens, allergens, or combinations thereof, is in a depot at the junctional epithelium of the gingival crevice.

3. The device of claim 1, wherein the effective amount of one or more antigens, immunogens, allergens, or combinations thereof includes one or more agents that increase permeability of the one or more antigens, immunogens, allergens, or combinations thereof into the gingival crevice.

4. The device of claim 1, wherein the effective amount of one or more antigens, immunogens, allergens, or combinations thereof deposited into the gingival crevice of the subject ranges from picograms to milligrams.

5. The device of claim 1, wherein triggering the immune response in the subject includes activating, modifying, or anergizing the immune response.

6. A method of triggering an immune response in a subject, comprising:

treating a surface of a floss by changing the surface energy of the surface of the floss to promote adhesion of one or more antigens, immunogens, allergens, or combinations thereof to the surface of the floss, wherein changing the surface energy of the surface of the floss includes exposing the surface to oxygen treatment, plasma treatment, or any combination thereof;

including one or more excipients to the one or more antigens, immunogens, allergens, or combinations thereof to enable controlled release of the one or more antigens, immunogens, allergens, or combinations thereof onto an apical aspect of a gingival crevice for absorption through a junctional epithelium of the gingival crevice;

one or more of embedding, coating, and attaching an effective amount of the one or more antigens, immunogens, allergens, or combinations thereof onto the treated surface of the floss; and configuring a combination of a thickness of the floss and a thickness of the effective amount of the one or more antigens, immunogens, allergens, or combinations thereof to be 500 microns or less to enable the floss to reach the junctional epithelium at the apical aspect of the gingival crevice;

inserting the floss into the gingival crevice with sufficient depth to reach the junctional epithelium at the apical aspect of the gingival crevice; and depositing, in response to reaching the junctional epithelium at the apical aspect of the gingival crevice, the effective amount of the one or more antigens, immunogens, allergens, or combinations thereof for absorption through the junctional epithelium of a gingival crevice of the subject, while excluding absorption through the vestibular mucosa, to obtain one or more of a mucosal and systemic immune response in the subject.

7. The method of claim 6, wherein at least one of:

the one or more antigens, immunogens, allergens, or combinations thereof are provided to maximize delivery of the one or more antigens, immunogens, allergens, or combinations thereof into the gingival crevice;

the one or more antigens, immunogens, allergens, or combinations thereof are provided repeatedly to a junctional epithelium of the gingival crevice;

the one or more antigens, immunogens, allergens, or combinations thereof is applied once or more than once with a frequency on a daily or weekly or monthly basis, such as 1, 2, 3, 4, 5, or 6 times daily or 1, 2, 3, 4, 5, 6, or 7 times weekly or 1, 2, 3, or 4 times monthly;

the one or more antigens, immunogens, allergens, or combinations thereof desensitize an individual to the antigens, immunogens, allergens, or combinations thereof by 10%, 20%, 30%, 40%, 50%, 60%, 70%, 80%, 90% or 100%;

the one or more antigens, immunogens, allergens, or combinations thereof trigger the immune response in the subject to the antigens, immunogens, allergens, or combinations thereof by between 0.1-100% to protect the subject to the one or more antigens, immunogens, or combinations thereof, or wherein between 0.001%-100% of the one or more antigens, immunogens, allergens, or combinations thereof, is in a depot at the junctional epithelium of the gingival crevice.

8. The method of claim 6, wherein the effective amount of one or more antigens, immunogens, allergens, or combinations thereof includes one or more agents that increase permeability of the one or more antigens, immunogens, allergens, or combinations thereof into the gingival crevice.

9. The method of claim 6, wherein the effective amount of one or more antigens, immunogens, allergens, or combinations thereof deposited into the gingival crevice of the subject ranges from picograms to milligrams.

10. The method of claim 6, wherein triggering the immune response in the subject includes activating, modifying, or anergizing the immune response.

* * * * *